(12) United States Patent
Bardo

(10) Patent No.: US 11,857,465 B2
(45) Date of Patent: Jan. 2, 2024

(54) PORTABLE COLLAPSIBLE AIR ISOLATION APPARATUS

(71) Applicant: Michael Bardo, Winnetka, CA (US)

(72) Inventor: Michael Bardo, Winnetka, CA (US)

( * ) Notice: Subject to any disclaimer, the term of this patent is extended or adjusted under 35 U.S.C. 154(b) by 0 days.

(21) Appl. No.: 17/948,133

(22) Filed: Sep. 19, 2022

(65) Prior Publication Data
US 2023/0015948 A1    Jan. 19, 2023

Related U.S. Application Data

(63) Continuation of application No. 17/246,715, filed on May 2, 2021, now Pat. No. 11,446,194.

(60) Provisional application No. 63/023,250, filed on May 12, 2020.

(51) Int. Cl.
  *A61G 10/00*  (2006.01)
  *A61M 5/14*  (2006.01)
  *A61G 10/02*  (2006.01)

(52) U.S. Cl.
  CPC ......... *A61G 10/005* (2013.01); *A61G 10/023* (2013.01); *A61M 5/1415* (2013.01)

(58) Field of Classification Search
  CPC . A61G 10/005; A61G 10/023; A61M 5/1415; A61M 5/1417
  USPC .................................................... 600/21–22
  See application file for complete search history.

(56) References Cited

U.S. PATENT DOCUMENTS

| | | | |
|---|---|---|---|
| 6,461,290 B1* | 10/2002 | Reichman | A61G 10/005 5/6 |
| 6,508,850 B1* | 1/2003 | Kotliar | A61G 10/005 55/385.2 |
| 11,071,671 B1* | 7/2021 | Theriault | A61G 10/005 |
| 2004/0255937 A1* | 12/2004 | Sun | A61G 10/00 128/201.25 |
| 2006/0247487 A1* | 11/2006 | Arts | A61G 11/009 600/21 |
| 2007/0056593 A1* | 3/2007 | Kubicsko | A61F 5/3769 128/846 |
| 2013/0204074 A1* | 8/2013 | Belval | A61G 11/009 600/22 |
| 2014/0090680 A1* | 4/2014 | Reis | A61G 1/017 135/96 |
| 2015/0231012 A1* | 8/2015 | Rapoport | A61G 11/006 29/428 |
| 2016/0074268 A1* | 3/2016 | Breegi | A61G 11/009 600/21 |
| 2016/0151218 A1* | 6/2016 | Canty | A61G 7/047 600/21 |
| 2017/0145711 A1* | 5/2017 | Esses | E04H 15/008 |
| 2019/0380901 A1* | 12/2019 | Breegi | A61G 11/009 |
| 2021/0298979 A1* | 9/2021 | Klein | A61G 10/023 |
| 2021/0307872 A1* | 10/2021 | Vizulis | A61G 10/005 |
| 2021/0307985 A1* | 10/2021 | Staab | A61G 12/00 |

(Continued)

*Primary Examiner* — Sunita Reddy
(74) *Attorney, Agent, or Firm* — Chris J. Zhen

(57) ABSTRACT

A collapsible air isolation apparatus is disclosed. The apparatus may include a collapsible frame including a base and a set of rigid panel or soft elements at least partially enclosing a volume of space, where each of the set of rigid or soft panel elements is foldably hinged to at least one of the base or another of the rigid or soft panel elements, and where at least one panel element of the set of rigid or soft panel elements includes an open space for mounting a motor for moving air. The apparatus may include mounting system attached to the base.

14 Claims, 18 Drawing Sheets

(56) References Cited

U.S. PATENT DOCUMENTS

| | | | |
|---|---|---|---|
| 2021/0307987 A1* | 10/2021 | Mosser | A61G 10/02 |
| 2021/0317679 A1* | 10/2021 | Hornick | E04H 15/48 |
| 2021/0322243 A1* | 10/2021 | Hamilton | A61G 1/04 |
| 2021/0338361 A1* | 11/2021 | Majzoub | A61B 46/20 |
| 2021/0338509 A1* | 11/2021 | Clendenin | A61G 10/005 |
| 2021/0386604 A1* | 12/2021 | Moore | A61B 90/05 |
| 2022/0001216 A1* | 1/2022 | Adams | A61G 10/023 |

* cited by examiner

PORTABLE COLLAPSIBLE AIR ISOLATION APPARATUS

CROSS-REFERENCE TO RELATED APPLICATION

This application claims the benefit of U.S. patent application Ser. No. 17/246,715 filed May 2, 2021, entitled "PORTABLE COLLAPSIBLE AIR ISOLATION APPARATUS" which claims the benefit of U.S. Provisional Patent Application No. 63/023,250 filed May 12, 2020, which are incorporated by reference herein in their entirety.

BACKGROUND

Field

The present disclosure relates to the field of devices for isolation of airborne pathogens, and more particularly to portable devices for use with patients in isolating the airborne pathogens.

Background

In recent years there have been incidences of viral outbreaks including ones with pandemic effects, with such viral outbreaks including the H1N1 virus, SARS-CoV and SAR-CoV-2 spreading throughout the globe. In addition, the world is facing increases in drug-resistant strains of pathogenic organisms.

Existing devices used for these and other problems have failed to address the needs of health care professionals and patients. Some devices have provided for enclosing the air space of a patient; however, these devices have drawbacks. Some existing devices are bulky, taking up significant space and being difficult to deploy due to the bulk of the devices. Some other devices have been too flimsy or lack good visibility for the health care professionals to visually monitor the patients. Some of the existing devices, however are expensive, difficult to deploy, or otherwise fail to meet the needs for large rapid development. Some devices fail to properly contain the infectious airborne particulates within the contained environment.

There is an increasing need for improved devices that help to reduce or isolate pathogens between a healthcare provider and a patient that is convenient to deploy.

Accordingly, there is a need for an improved isolation device that addresses the threats of increasing infectious outbreak that is also suitable for mass deployment.

SUMMARY

In an aspect of the disclosure, a collapsible air isolation apparatus is disclosed. The apparatus may include a collapsible frame including a base and a set of rigid panel elements at least partially enclosing a volume of space, where the set of rigid panel elements is foldably hinged to at least one of the base or another of the rigid panel elements, and where at least one panel of the set of rigid panel elements comprises an open space for mounting a motor for moving air. The apparatus may include the motor for moving air configured to create a negative pressure within the volume of space of the collapsible frame.

In another aspect of the disclosure, a method for treating a person using a collapsible isolation apparatus is disclosed. The method may include providing the collapsible isolation apparatus including a collapsible frame including a base and a set of rigid panel elements at least partially enclosing a volume of space, where the set of rigid panel elements is foldably hinged to at least one of the base or another of the rigid panel elements, and where at least one panel of the set of rigid panel elements includes an open space for mounting a motor for moving air. The method may include assembling the collapsible isolation apparatus by folding out the plurality of rigid panel elements into an assembled configuration. The method may include providing the person treatment using the collapsible isolation apparatus. The method may include placing and orienting the person within the collapsible isolation apparatus.

DETAILED DESCRIPTION

Figure 1:
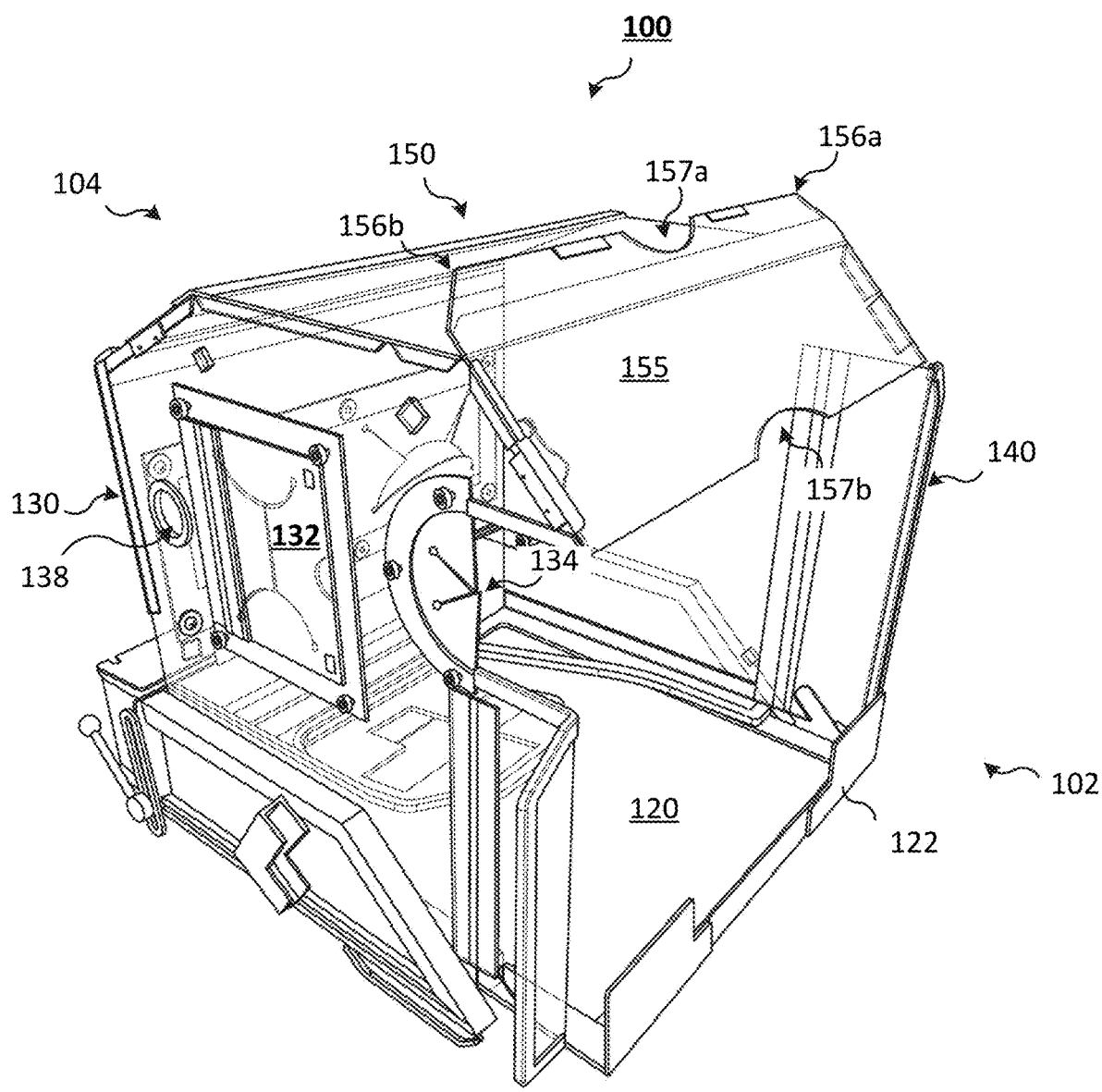
FIG. 1 is a perspective view of an exemplary portable collapsible air isolation apparatus for treatment of patients with respiratory symptoms, according to an embodiment of the disclosure.

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. It will, however, be apparent to those skilled in the art that these concepts may be practiced without these specific details. In some instances, well known structures and components are shown in block diagram form in order to avoid obscuring such concepts.

According to some health organizations, one concept of infection control is to prevent or stop the spread of infections in the healthcare setting. Separating or isolating infectious organisms from a clean environment by utilizing a physical barrier limits the spread of the infectious organism. Several aspects of an air isolation apparatus or box will now be presented with reference to various apparatuses and methods. These apparatuses and methods will be described in the following detailed description and illustrated in the accompanying drawings by various blocks, modules, components, steps, processes, etc. (collectively referred to as "elements"). While the methods may be described in an ordered series of steps, it will be apparent to those skilled in the art that the methods may be practiced in any operative order and each step may be practiced in various forms that are apparent to those skilled in the art. Air isolation apparatus, isolation apparatus, box, intubation box, isolation system, system, or simply apparatus may be used interchangeably in the disclosure. In some examples, patient isolation apparatus/structure/box/system may be used interchangeably with Air isolation apparatus. In some instances, these terms may refer to the entire system including the structure, and accessories such as an intravenous (IV) pole, filtration system, etc. In other instances, the terms may simply refer to the structure itself not including any or all of the accessories. Some exemplary measurements may be provided throughout the specification by way of example and not of limitation. When a numerical value and/or measurement is provided, it is understood that the dimensions may be smaller or larger according to preference or design requirements.

A portable collapsible air isolation apparatus may be versatile, yet provide a portable protective barrier enclosure designed to prevent an operator of the apparatus and their equipment from exposure to pathogenic biological airborne particulates, such as SARS-CoV-2, an infectious respiratory virus. In some embodiments, the apparatus may provide a non-permeable physical barrier that effectively separates infectious aerosolized droplet particles from the surrounding environment, by containing the patient's infectious droplets within its micro-environment. An operator may be used interchangeably with health care provider. Health care provider may include, without limitation, practitioners, including physicians, physician assistants, pharmacists, dentists, nurse practitioners, nurses, respiratory therapists, paramedics, emergency medical technicians, physical therapists, technologists, dental assistants, or any other practitioners or allied health professionals, etc. that have a role in using a device for human use. "Operator" may be one or more of any combination of health care practitioners. This medical device may be a transparent physical barrier designed to cover a patient's head and upper body that incorporates access ports, sealed by Federal Drug Administration (FDA)-grade silicone rubber, to allow for isolated patient access through which the operator's hands may be passed to perform medical procedures. Due to its mobile capability, the protective barrier enclosure may be utilized by first responders upon the initial point of contact with a confirmed infectious, or suspected to be infectious, patient. By isolating a patient from the initial point of contact, the risks of spreading deadly diseases such as SARS-CoV-2, through aerosolization and fomite transfer may be significantly reduced. Those skilled in the art will recognize that the description provided herein is by way of example and of limitation. In other embodiments, the air isolation apparatus may be used with robots or remote-controlled robotic systems. In yet other embodiments, the air isolation apparatus may be used in mixed environments with a mixture of human attendants (operators) and machinery or robotic systems. For example, robotic systems may provide for routine or pre-programmed procedures on a patient through the air isolation apparatus, while humans may provide specialized procedures (either before or after the robotic assistances).

In some embodiments, the apparatus may provide an additional layer of barrier protection in addition to personal protective equipment (PPE) against airborne particles or droplets expelled from patients or the attending healthcare provider. In this manner, the apparatus may provide protection to one or both of the healthcare provider and the patient. While the apparatus may provide for significant protection, in some instances, the apparatus may not be intended to replace the need for PPE or room/equipment sanitation and disinfection procedures. Because the apparatus is portable and collapsible, the apparatus may be removed if to avoid impeding an operator's ability to care for a patient or impeding the operator's ability to perform a medical procedure on the patient. The patient may be under direct observation and receive supplemental oxygen via portable or wall-mounted medical air during use of the apparatus.

The design of the apparatus may provide fast and speedy deployment based on the foldable configuration that allows the apparatus to be deployed in a few easy steps. As well, the apparatus may be folded up when the operator is finished with use of the apparatus. Fast deployment provides significant benefits to both the patient who can receive immediate care, while also provide benefits to the operators who will be protected from possible pathogens from the patient. Another benefit of the design may include safety in deploying the apparatus and safety in usage of the apparatus. The apparatus may also be designed with the features of portability and versatility.

In one embodiment a gurney attachment system may be provided for enhancing the functions of the apparatus. In some embodiments, the gurney attachment system may be a proprietary system design to be suitably used with the apparatus. The gurney attachment system may include two components of an anchor and a brace. Together, the anchor and brace allow the apparatus to be quickly attached to most gurneys and hospitals beds, and to be safely used during transport of a patient, decreasing chances of injury to the patient or operator. The brace may also prevent the apparatus from sliding forward and down when the head of the gurney or bed is elevated to Fowler's position (e.g., a standard patient position where the patient may be seated at any angle including 45-60 degrees), allowing the patient to sit upright and breathe more comfortably.

In one aspect, the apparatus may be configured as a proprietary multi-purpose apparatus with ample interior space for working with the patient. The apparatus may be configured to contain the spread of infectious aerosolized droplets within a small footprint, while still allowing ample room for an operator to freely maneuver medical instruments inside of the apparatus. In another aspect, the apparatus may be configured to provide safe access to a patient without physical restrictions. The wide main access panel may allow the operator to have unrestricted access to the patient including the patient's cephalic region, providing the operator with sufficient range-of-motion to render various life-saving medical procedures or treatments without the typical constraints associated with an intubation box.

In some embodiments, the apparatus may include a self-sustaining filtration system that allows the apparatus to be used for any duration including long durations. For example, by supplying a 3M® HEPA filtration system, the apparatus may be able to sustain its own negative-pressure micro-environment, without the need of an external source of suction (e.g., a hospital suction line), for up to eight hours or more as a patient is being transported. In some embodiments, the filtration system may be powered (e.g., battery or electricity powered) using any number of filter elements; in other embodiments, the filtration system may be a passive (non-powered) system.

A storage box found on the operator side (e.g., the side used by an operator to serve the patient) of the unit may allow for convenient access and protection of all the mechanical filtration components, as well as an IV Pole. The apparatus provides many benefits including early isolation. Isolating a patient with infectious or potentially infectious aerosolized droplets and other pathogens from the first point of contact in the field may significantly reduce the risk of inadvertently spreading a deadly respiratory disease, such as SARS-CoV-2. Another benefit may include durability of the embodiments. The apparatus may be comprised of lightweight and durable aluminum, which provides a structural framework for the flexible and highly impact resistant polycarbonate panels that may compose the apparatus. One or more panels may form a frame of the apparatus. One skilled in the art will recognize that materials may vary based on design or user preference. While some embodiments show rigid panels and structures, the disclosure is not so limited. In some examples, non-rigid structures and materials may be used where suitable based on user preference or design. In other embodiments, the materials may be selected from any variety of metals, woods, plastics, polymers, ceramics, glass, hybrids, etc. Non-rigid materials may be used where suitable, with such materials including fabrics/textiles (whether natural or synthetic), foams, etc.

Another benefit of the embodiments may include providing access to various points of the patient. For example, the apparatus may include holes or openings at any of the surfaces including the top, side, rear (facing from the open side). For example, the apparatus may be equipped with various access points (e.g., main access panel, auxiliary access panel and semi-circular arm port) which may allow first responders and operator to safely, properly, and effectively render the vital care a respiratory-compromised patient may require.

The apparatus may enable a patient-focused perspective. For example, multiple respiratory treatment modalities may be utilized. By allowing operator and first-responders to safely perform aerosol generating procedures (AGP) such as intubation, emergency continuous positive airway pressure (CPAP), bi-level positive airway pressure (Bi-PAP), high flow nasal canula (HFNC), and nebulized breathing treatments out in the field, a patient's chances of survival may be significantly increased due to the earlier onset of medical care received. As well, the apparatus provides the ability to render necessary life-saving treatments/procedures earlier on during the course of infection that may significantly increase a patient's chances of survival.

Yet another benefit of the apparatus may be lowering costs by keeping healthcare employees safe, preventing the spread of germs and pathogens, decreasing costs on cleaning supplies, and potentially decreasing staff call-outs.

In the various embodiments, some features of the apparatus may include a foldable design, with an apparatus that may fold down to a height of five inch or less; other embodiments may fold to a taller height based on design or preference. Another feature may include a collapsible design, with the apparatus being able to be collapsed in as few as ten seconds or less; other embodiments with increased features or based on design or preference may fold in greater than ten seconds. Yet another feature may include fast and speedy assembly, with the physical barrier that may be quickly assembled in ten seconds or less; other embodiments with increased features or based on design or preference may be assembled in greater than ten seconds. Some embodiments may include generous interior dimensions providing ample room for an operator to comfortably perform necessary procedures/treatments without the typical constraints of other embodiments. Yet another feature may include fast and speedy full apparatus assembly, including assembly of the entire system which may include the apparatus, motor with filter (e.g., a 3M® motor with HEPA filter), and clear drape which may together be assembled in at little as one and a half minutes or less; other embodiments with increased features or based on design or preference may be assembled in greater than one and a half minute. While the disclosure includes a motor in some embodiments, those skilled in the art will recognize that any variety of mechanisms to provide negative pressure may be used, including the motors, other electro-magnetic systems, induction systems, fans, blower motors, or any other mechanical or hydraulic type system, etc.

Another feature may include a portable design including preset mounts which may be in place with attachment elements (such as carabiners) for a shoulder strap, as well as a conveniently placed carry handle. Another feature may include a stackable design, wherein when multiple apparatuses are stored together, they may be stacked on top of each other, and the central safety catch of the apparatus on top (of each corresponding pair of apparatuses) will interconnect through a slit that is located at the top of the corresponding bottom apparatus. Another feature may include a versatile design including an apparatus able to be deployed and safely operated on any standard gurney or hospital bed with (e.g., any size including from two inch to six inch mattress thickness) without interfering with the transport and maneuvering of the gurney or hospital bed. Another feature may include being self-contained and self-sustaining, with the apparatus supplying its own intravenous (IV) pole (e.g., to hang IV fluid bags), as well as a 3M® motor, HEPA filters, and a battery (which may include an intrinsically safe battery with up to eight hours or more of battery life). Another feature may include a re-usable design with any or all components being re-usable between patients after proper disinfection; in some embodiments the drape (e.g., a clear plastic drape, fabric, etc.) may be a one-time use item. In some embodiments the reusable components may be disinfected with a variety of cleaners including hydrogen peroxide, soap, water, bleach (including in diluted form), as well as Sani-Cloth®. The apparatus may include panels with transparent or see-through material such as plastics, polycarbonates, glass, etc., which may be durable and highly impact resistant. In some embodiment, the apparatus may use panels having a thickness of up to ⅛" or 1/16" or greater. The apparatus may be hinged (e.g., using piano or spring hinges) at the base and/or other edges. When the apparatus is assembled, the edges may be sealed (e.g., with polycarbonate channels) to ensure that the infectious aerosolized droplets do not escape to the surrounding environment. Alignment of the panels may be achieved through various means including using any combination of tabs, neodymium magnets, velcro, latches, etc. to keep the center panels properly aligned over the bilateral side panels while also maintaining its shape. The apparatus may be disinfected with a variety of cleaners including: hydrogen peroxide, soap & water, bleach (e.g., 10:1 dilution), and Sani-Cloth®.

Some embodiments may include unique custom designs including magnet channels and methods of attachment. There may be custom stainless steel magnet channels (in some examples there may be eight such channels) that are designed to hold and channel both the north and south poles of an N52 neodymium bar magnet in one direction, towards a stainless-steel strike plate. All stainless-steel parts may be passivated for extra corrosion resistance.

In some embodiments, there may be two magnet channels that are located towards the base of the apparatus, with one attached to the frame via the square aluminum tubes located on each side. The two corresponding strike plates for these magnets may be attached to the outside of each of the side panels. These magnets may serve to maintain the stability of the side panels as well as aid with keeping them erect and aligned when the apparatus is being setup and assembled.

In some embodiments, there may be two magnet channels that are located on the vertical backing plate with its corresponding strike plates located towards the base of the front panel. There may be two corresponding strike plates located on the back of the rear panel. These two magnet channels may have a dual purpose, which may be to maintain the stability of the front panel during assembly and use, as well as attaching to the rear panel when the apparatus is collapsed for storage to keep the apparatus from unintentionally opening.

There may be four magnets located at the bottom side of the apparatus, which serve to maintain the swing arms in position. They aid with keeping the swing arms in place when flipped forward to stay in position and maintain the protection of the edge of the polycarbonate apparatus that extends out. When the swing arms are flipped backward, and the apparatus is installed on a gurney or hospital bed, the magnets keep them stored in place. These magnets may also be replaced with spring hinges that are loaded to close (or biased/tensions to close).

The lid of the box may also be held by two small magnets, or two spring hinges loaded to close (or biased/tensions to close).

There may be four magnet channels that may be strategically placed on the top of both side panels, with one towards the operator side and one towards the patient's side, per panel. These four magnet channels may be held in place on the polycarbonate panels via two roll pins that penetrate the layers of material (e.g., three layers), which may consist of two layers of the stainless-steel channel and the polycarbonate panel sandwiched in between, firmly holding them in place. Four strike plates which may have a similar design with the roll pins for attachment, may be located on the far lateral sides of the lid/center panels and correspond to the location of the magnet channels. This system may keep the center panels properly aligned over the bilateral side panels and maintain the apparatus's shape and rigidity throughout use. These magnets may prevent the lid from slipping and collapsing down towards the patient during use or transport.

In some embodiments, the apparatus may include a cover or drape over some or all the structure. In some embodiments, the cover(s) may be designed to be draped over the top of the apparatus via the rear panel, tucked over areas of the patient's body (e.g., including the caudal region), around the shoulders and arms, and then non-permanently locked inside two tension locks found on both sides of the apparatus. The drape may create a seal around the patient's upper body, containing any infectious aerosolized droplets that may escape, and complements the apparatus structure and filtration system in creating a negative pressure microenvironment. For example, the filtration system may create negative pressure (i.e., the pressure inside of the apparatus is lower than the pressure outside) within the apparatus so that germs do not escape the inside into the outside environment. In some embodiments, the seal around the patient's thoracoabdominal region may not be air tight, which allows a sufficient influx of ambient air to enter and move towards the apparatus as the filter motor and filter draw contaminated air out of the apparatus, filtering it in the process. The drapes may allow operators and first responders to safely perform cardiopulmonary resuscitation (CPR), while still being protected from the patient's infectious or potentially infectious aerosolized droplets that are being compressed out upon exhalation while they are performing chest compressions.

The base may be made up of a lightweight frame material such as aluminum with certain components made up of stainless steel, such as the IV pole and IV pole base, as well as the mechanism that attaches the proprietary anchor and brace system. In some embodiments, the base may maintain the structure and rigidity of the apparatus when it is fully assembled. The base may be the unifying structure which allows the apparatus to be safely adapted for use on gurneys and hospital beds via its attachment to the anchor, brace, and accessory components. The accessory components may include any or all of the components other than the main structure; in some embodiments, the accessories may include the IV pole, motor, filtration system, drapes, etc. The configuration may also provide protection and easy transport of the collapsed polycarbonate panels, filtration system, and accessory components.

In some embodiments, the apparatus may include an IV pole, as well as a filter motor (e.g., a 3M® filter motor), HEPA filters, and an intrinsic battery (e.g., one lasting up to 8 hours or more). This configuration may allow the negative pressure micro-environment to be maintained throughout the transportation of a patient on a gurney/hospital bed, without the need of an external source of suction (such as a hospital's suction line).

FIG. 1 is the apparatus 100 as viewed from the patient's side 102 with the operator's side left panel 104 towards the far left end.

For reference, when viewed from the operator's perspective 104, the panel 130 is the "right" panel, and panel 140 is the "left" panel.

The apparatus may include three access points, with the one access panel (e.g., a main access panel) (at the back from the patient's perspective 102 or front from the operator's perspective 103) of the apparatus 100 having the largest opening; in some embodiments the main access panel (obscured in FIG. 1). The auxiliary access panel 132 may measure 6" wide×8" tall and may be custom installed depending on provider preference on the left and/or the right side panel 130, 140. This auxiliary access panel 132 may permit an operator/assistant to quickly and safely introduce necessary equipment that the operator may require, such as a stylet, bougee, laryngoscope, endotracheal tube, emergency CPAP device, bag-valve mask (BVM), or to provide assistance. Another opening, arm port 134, (which may also be called the third access point) may be a semi-circular arm port 5" in diameter, which allows an operator/assistant to safely insert their arm into the apparatus 100 to continue with life-saving bag-valve mask (BVM) compressions without completely breaking the seal formed by the clear plastic drape. The main and auxiliary access panels 132 may be designed to self-close and may be kept sealed in place by an attachment mechanism including magnets, Velcro, latches, snap fastener, etc. Both panels 132 and the arm port 134 may be lined by Food & Drug Administration (FDA) grade silicone rubber which may have cutouts to accommodate the operator's arms. The silicone rubber templates may be held in place by a polycarbonate frame, which may be attached via thumbs screws, allowing them to be quickly replaced as needed. While the embodiment of FIG. 1 shows rubber flaps in the openings auxiliary access panel 132, arm port 134, those skilled in the art will recognize that various suitable designs may be used based on preference and requirements. For example, in some embodiments, the openings auxiliary access panel 132, arm port 134 may be coupled to long gloves (e.g., also used in glove boxes) such that there are no air gaps or holes. Yet other embodiments are possible using other elastic or flexible materials.

The panel 130 may include an access port 138 to install a motor (not shown) that may be used for filtering air and/or to create a negative pressure within the apparatus 100. Such port may be called a suction port. In some examples, such as illustrated in FIG. 1, the access port 138 may be a circular port lined with a rubber grommet to install the motor. The motor may draw air out of the space within the apparatus 100. In some embodiments, the motor may be a 3M® HEPA filter motor. In some embodiments, the motor may be fixed and/or permanently attached to a panel 130, 140 with air gaps minimized using sealing material.

In some embodiments, the opposite side 140 (right side from patient's perspective 102) may be similarly designed and a mirror image of the left side 130, including an auxiliary access port and/or arm port. In some embodiments, the oppose side 140 may or may not include the motor port 138. The left 130 and right 140 sides may include any combination of the access ports based on user preference and design. For example, in some embodiments on the left panel 130 includes access ports; in other embodiments, only the right panel 140 includes access ports. In yet other examples, there may be one access port on one side and two access ports on the other side. Any number and type of ports may be present on either panel 130, 140.

Figure 2:
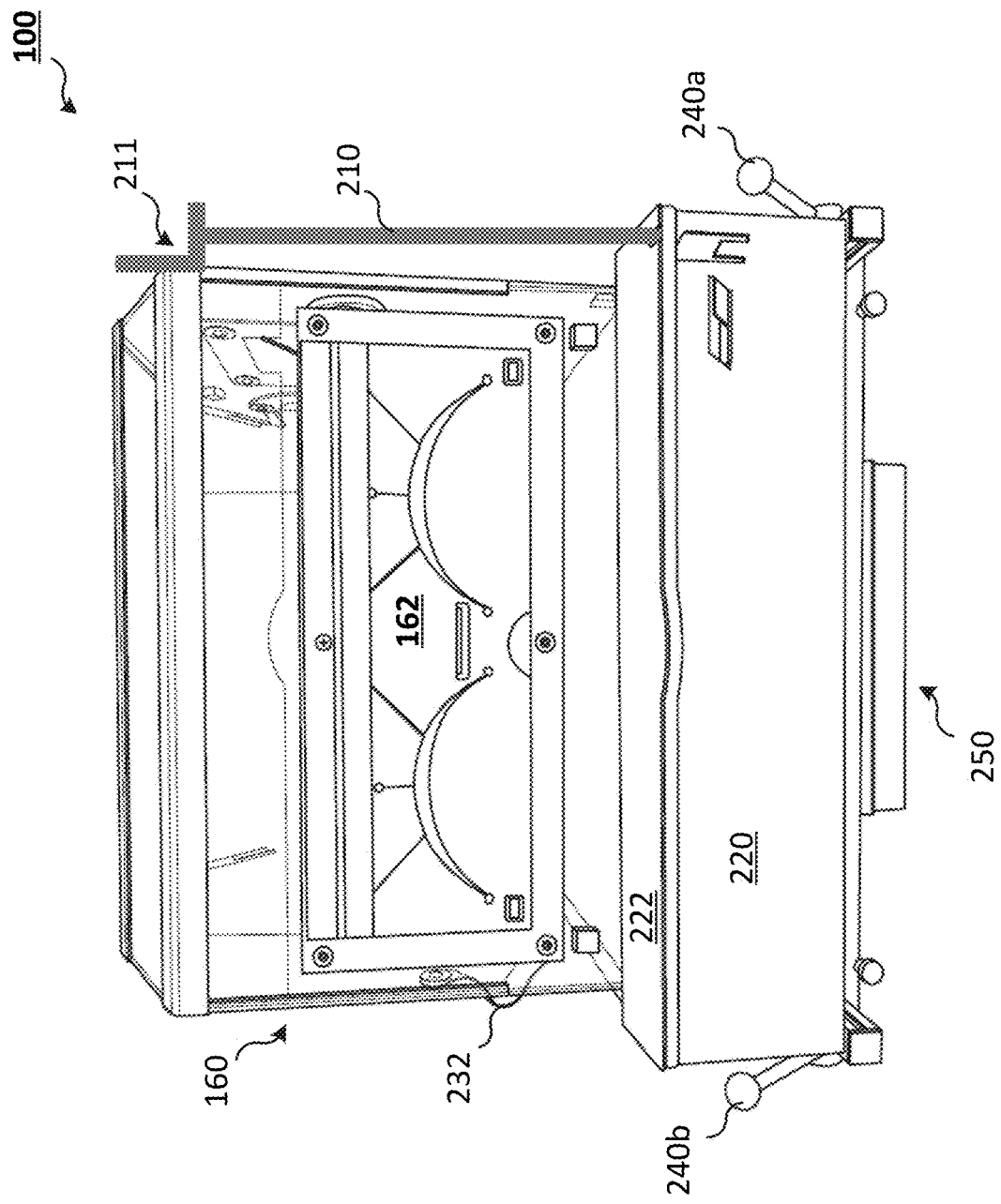
FIG. 2 is a view of the exemplary apparatus as viewed from the operator's perspective, according to an embodiment of the disclosure.

In some embodiments, the panel 155 may have two bilateral corners 156a-b (e.g., at 45 degrees) located at the top left and top right of the panel 155. This design may prevent the sharp corners from tearing into the drape (e.g., clear plastic drape not shown) that is installed on the apparatus 100. It may also allow the drape to be easily folded upon itself along the edge, forming a "buffer-zone" that contributes to the seal of the apparatus 100. As illustrated in FIG. 2, there may be two semi-circular cutouts 157a-b at the midline of the rear panel. The cutouts may allow the operator to easily reach through the rear panel 160 to collapse the apparatus.

Some embodiments may include the protective shield 122. When the apparatus 100 is collapsed and not in use, the L-shaped protective shield 122 may be flipped forward into position (as shown in FIG. 1) to protect the underside of the apparatus 100 and its flex panel deflectors. Before the apparatus 100 is fully deployed and attached to a gurney or hospital bed, this protective shield may be released and pulled back towards the operator before use. This shield 122 may be swung back towards the operator, and the base 120 is placed on top of a gurney or hospital bed. The shield 122 may serve a secondary function by helping to stabilize any left and right swaying movement of the apparatus that may occur while on the gurney or hospital bed.

FIG. 2 is a view of the exemplary collapsible apparatus 100 as viewed from the operator's perspective. The panel 160 may be called the "rear" panel if seen from the patient's perspective or the "front" panel if seen from the operator's perspective.

As described above, on either one of the side panels 130, 140 may be included an auxiliary access panel, semi-circular arm port, and a two-inch access port lined by a rubber grommet, for placement of a motor and filter. The panel that does not contain the auxiliary access panel, semi-circular arm port, and two-inch access port, may have a six-inch fiberglass reinforced rubber silicone handle 232 attached to it, e.g., via two barrel bolts. The handle 232 may be placed towards the operator and in the lower half of the panel 140. The handle 232 may provide for ergonomic accessibility when lifting the panel upwards to assemble.

Some embodiments may include an IV pole 210. The IV pole 210 may be made out of metals or other solid materials including stainless steel (e.g., 304 stainless steel) providing for high corrosion resistance. The IV pole 210 may be attached to the storage box 220 through a uniquely designed hook and slot system that allows the IV pole 210 to be secured safely when not in use as well as when it is erected vertically with an IV bag attached (not shown). The specially designed hook and slot system may prevent the IV pole 210 from coming apart from the component storage box 220 while the apparatus is being transported. The apparatus 100 may utilize the weight of the attached base of the apparatus and gravity to keep the hook stabilized in the slot, unless it is manually lifted up and pushed forward out of the horizontal slot, sliding it out of the adjacent opening. Once the IV pole 210 clears the slot, it may be rotated 90 degrees to the right, and the reverse operation may be performed. The same hook on the IV pole 210 may be slipped forward through the vertical slot located about an inch away, then the IV pole 210 may be allowed to slide down the angle of the slot, into an adjacent slot on the right. The adjacent slot may prevent the hook from being pushed back out of the slot, unless the entire IV pole 210 is lifted up and slid to the left against the angled slot and out of the first slot. Once the IV pole 210 is in the vertical position and ready to be used, the lid 222 of the storage box 220 is closed, and contains another slot that wraps around the IV pole 210 itself. The slot in the lid further prevents the IV pole 210 from swinging/swaying while the gurney is in motion, and in the back of an ambulance. The slot in the lid 222 prevents any initial motion that could aid with the unwanted slipping of the hook up and out of the secured position. In addition to the slots that secure the IV pole 210 in place, there may also be a stainless-steel base attached at the bottom of the IV pole 210, which may act as a counterbalance, and aid with securing the IV pole 210 by preventing it from getting unintentionally knocked upwards during transport over bumps.

The embodiment may prevent unwanted and unintentional movement of the IV pole 210 while it is in the functioning, vertical position, as well as in the stored, horizontal position.

In some embodiment, the top of the IV pole 210 may have an L-shaped, 90-degree angle hook 211 that IV bags can be placed on. The IV pole 210 and IV hook 211 may be made of standard sized ⅜" diameter stainless steel rods, which may be highly corrosion resistant. The IV hook 211 diameter may be universal, allowing for the attachment of any standard medical IV bag. Those skilled in the art will readily recognize that any of a variety of mechanisms may be used to secure the IV bag or to provide hydration to the patient. In some embodiments where the IV bag or hydration is not necessary, the IV pole 210 may be omitted for configurations of the apparatus 100, or the IV pole 210 may be folded away in cases where the IV pole 210 is included in the configuration of the apparatus 100. In some embodiments, the IV pole 210 may be an integrated and/or permanently attached component of the apparatus 100 with a folding mechanism that easily folds out of the way and folds into the extended configuration.

In some embodiments, the IV hook 211 may accommodate a liter bag of IV fluids, while other embodiments may accommodate more than one bag of smaller volume medications/fluid bags.

Shown on FIG. 2 are knobs or handles 240a-b for adjusting the mounting system of the apparatus 100. A gurney/bed attachment mechanism 250 is also shown. The attachment mechanism 250 is used to secure the apparatus 100 to the gurney and/or bed. Those skilled in the art will recognize that other attachment mechanisms are possible as dictated by user preference or design. In other embodiments, the knob/handle 204a-b may be larger or smaller, round or other shape to cater to different users.

An operator may attend to a patient from an access port 162 (e.g., a main access port) that includes multiple hand openings on the panel 160. In some embodiments, this access port 162 may measure 18" wide×6" tall. This opening 162 may allow the operator to have unrestricted access to the patient's cephalic region, providing the operator with ample room to perform various life-saving procedures without many typical constraints. The access port 162 may be designed to self-close and may be kept sealed in place by an attachment mechanism including magnets, Velcro, latches, snap fastener, etc. The access port 162 may be lined by FDA grade silicone rubber which may have cutouts to accommodate the operator's arms. The silicone rubber templates may be held in place by a polycarbonate frame, which may be attached via thumbs screws, allowing them to be quickly replaced as needed. As with the auxiliary ports 134 (FIG. 1), in some embodiments, the access port 162 may be coupled to long gloves (e.g., also used in glove boxes) such that there are no air gaps or holes. Yet other embodiments are possible using other elastic or flexible materials.

Figure 3:
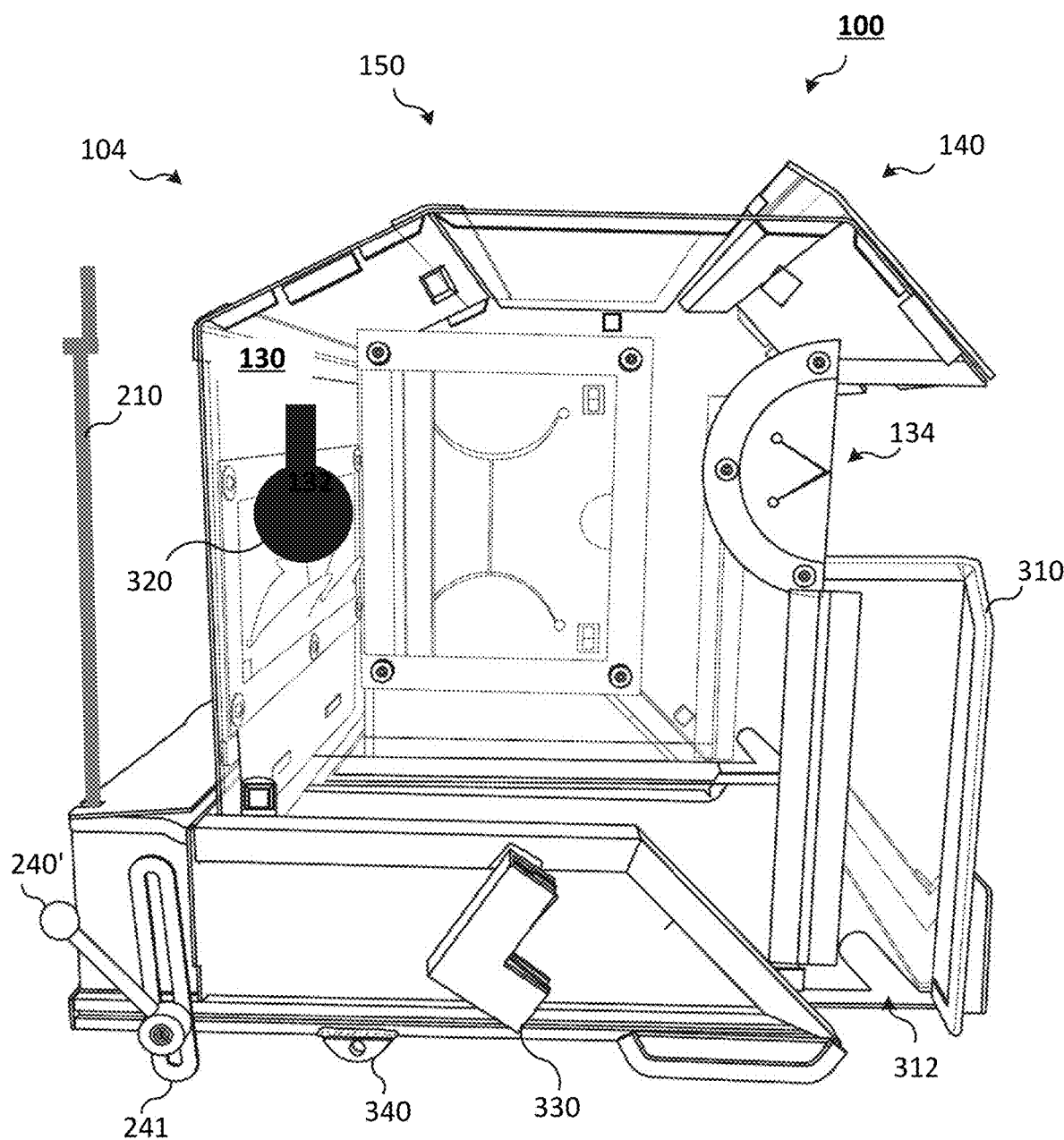
FIG. 3 is side view of the exemplary apparatus, according to an embodiment of the disclosure.

FIG. 3 is side view of the exemplary apparatus 100, according to an embodiment of the disclosure. The apparatus 100 may include bilateral flex panel deflectors 310 located on both sides of the apparatus 100 (opposite side of apparatus 100 may include similar deflector). The flex panel deflectors 310 may be attached to the apparatus 100 by hinges and allow for the comfortable accommodation of patients with wider shoulders. The flex panel deflectors 310 may aid in preventing free-floating aerosolized droplet particles from traveling out the sides of the apparatus 100. The flex panel deflectors 310 may be lined with rubber silicone to aid with gripping drapery that may be placed over the apparatus 100 including in the area of the deflectors 310. At the bottom of both flex panels may be ⅞" wide cutouts 312 (opposite side of apparatus 100 may include similar cutout) that are 2.2" long, and angled (e.g., around 47 degrees), towards the operator side. These cutouts 312 on both sides may allow for the safe passthrough of corrugated ventilation tubing (used when a patient is placed on a ventilator), oxygen tubing, IV lines, suction tubing, digital endoscope wires, and any other tubes/wires that may be used for the patient. These slots 312 may be angled (e.g., at around 47 degrees) to facilitate any emergency that could arise, requiring the entire apparatus 100 unit to be pulled backwards and away from the patient, at a slight (e.g., around 15 degree) angle. The angle may facilitate the tubes and wires to be dropped down and out of the way as the apparatus 100 is being pulled backward, preventing them from getting snagged on the apparatus 100, which could cause them to be pulled out from the patient, causing injury.

In the example of FIG. 3, the side panel 130 is shown with a motor 320 attached to the access port (138 of FIG. 1). The motor may include a hose or tubing extending from the motor for coupling to other hoses or tubing (not shown) to expel air from the apparatus 100. The IV pole 210 is shown installed to hang an IV bag in this configuration. Some embodiments may include a multi-purpose bracket 330

Loosening the mounting system knobs 240' on both sides may allow the loop slides 241 to freely slide up and down and rotate about the knobs 240'. It will be appreciated by those skilled in the art that the mounting system and loop slides may be implemented in any manner suitable for the embodiments.

Some embodiments may include a bilateral shoulder strap mount points 340, which may be attachment points located on both sides of the apparatus for carabiner attachments to a shoulder strap.

Figure 4A:
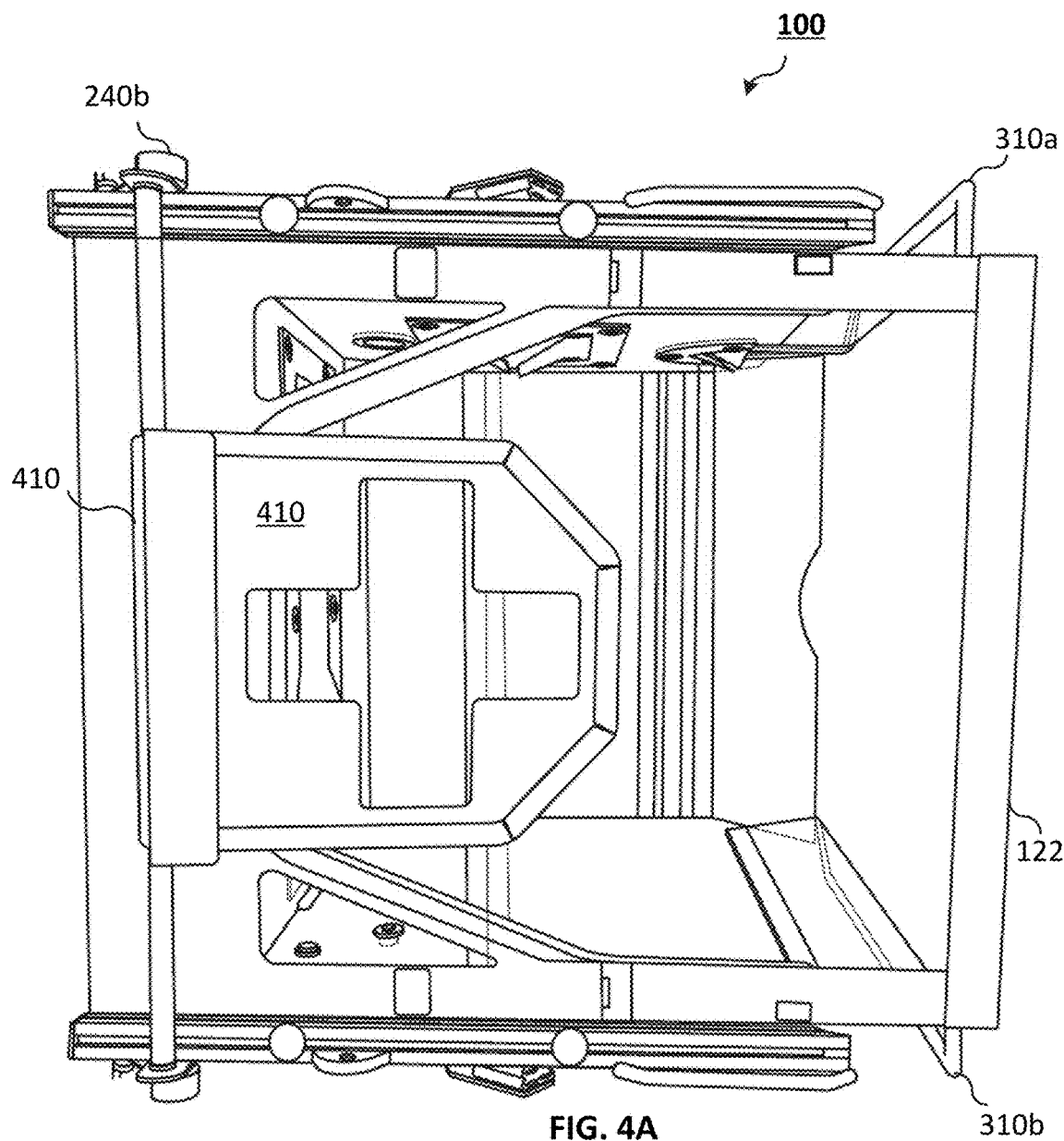
FIG. 4A is a bottom view of the exemplary apparatus, according to an embodiment of the disclosure.
Figure 4B:
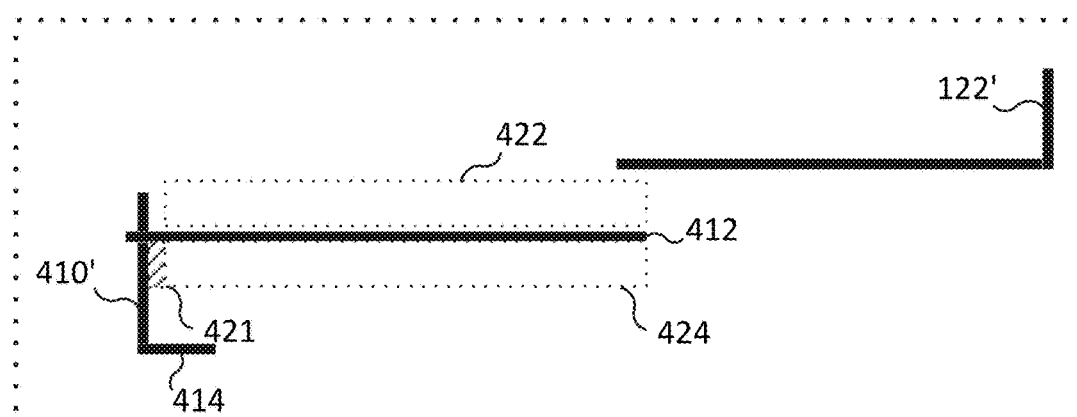
FIG. 4B is a side profile illustration of the gurney/bed coupling mechanism of FIG. 4A, according to an embodiment of the disclosure.
Figure 4C:
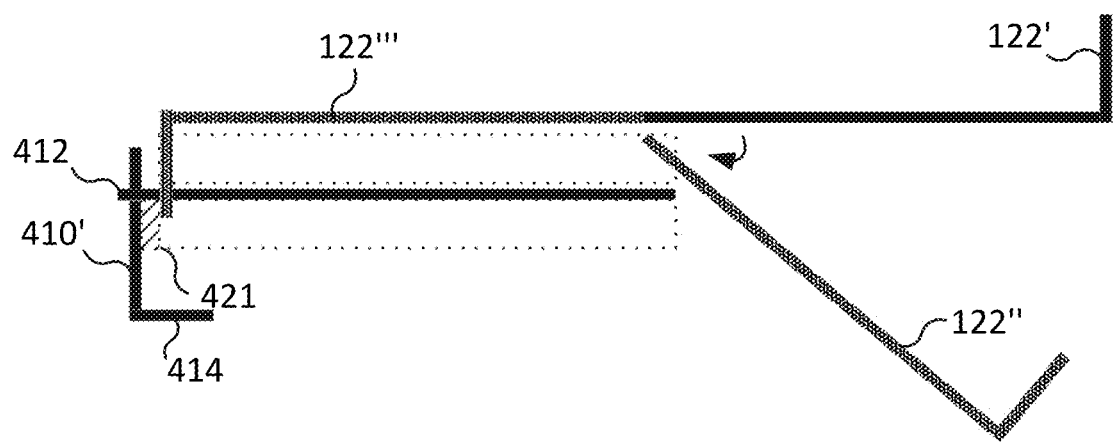
FIG. 4C is another side profile illustration showing rotation of the brace component, according to an embodiment of the disclosure.

FIGS. 4A-C are a bottom view (FIG. 4A) of the exemplary apparatus 100, a side illustration (FIG. 4B) of the brace 410, and an illustration (FIG. 4C) showing rotation of the brace, according to an embodiment of the disclosure. As seen from the bottom, the apparatus 100 includes the protective shield 122 (in the extended configuration). The protective shield 122 may serve another purpose of bracing the apparatus 100 against a gurney. The shield 122 may be called a brace 122. When the shield 122 is folded back, the shield 122 together with the coupling plate 410 combine to capture the frame 421 of the gurney 424 (a small section of a gurney is shown for illustrative purposes). The shield 122 pushes from the right side (as viewed from FIG. 4) while the coupling plate 410 pushes from the left side to capture the gurney frame 421. In some embodiments the coupling plate 410 may be called an anchor 410.

The coupling plate 410' may include a plate component 412 and a lower bracket component 414.

The knob 240, loop slide, anchor 410, and brace 122 may form the gurney attachment system (e.g., proprietary in some embodiments). The anchor 410 and brace 122 together may allow the apparatus 100 to attach non-permanently to the gurney 424 or hospital bed 422, mattress, padding, etc. (a small section of bedding is shown for illustrative purposes) without the use of a clamp or hook. The configuration may allow the apparatus 100 and base to be completely and immediately pulled away from the gurney 424 and patient in the event of an emergency. This may be achieved by having the operator grasp the L-shaped handles found on apparatus 100.

The anchor plate 410 may prevent the apparatus 100 from shifting back and forth, wobbling up and down, and swaying left to right while it is fully assembled on the gurney 424. The anchor 410 may be wedged in between the mattress 422 that the patient lies on, and the frame of the hospital bed or gurney 424. This may be a safety feature that prevents unintentional movement of the apparatus 100 while it is fully deployed with the patient inside the apparatus 100.

The brace 122 in conjunction with the anchor 410 may encase the top portion of the gurney 424 or hospital bed's 422 structural frame (towards the side of the patient's head), preventing the apparatus 100 from being unintentionally flipped backward and off of the patient while it is in use. There may be two red thumb screws located on the cross tube that connects the anchor 122 and brace 410 to the base that may be tightened once the apparatus 100 is fully assembled on the gurney 424, to prevent the tube from freely spinning. Tightening of these two red thumb screws as well as the two knobs that are on both sides of the base may keep the base and apparatus 100 sturdily attached to the gurney 424 or hospital bed 422 while it is in transport.

The brace 122 may function like a hook and prevent the apparatus from sliding forward and down when the head of the gurney 424 or bed 422 is elevated to Fowler's position, allowing the patient to sit upright and breathe more comfortably. The brace 122 may also assist with providing lateral stability by decreasing the amount of side-to-side rocking that may occur due to shifting of the patient's weight during transport, especially with the head of the gurney 424 or bed 422 elevated to Fowler's position. Together, the anchor 410 and brace 122 may allow the apparatus 100 to be quickly attached to most gurneys 424 and hospital beds 422 and to be safely used during transport of a patient, decreasing chances of injury to the patient, first responder, or operator.

FIG. 4C shows the movement/rotation of the brace 122' to capture the frame 421 of the gurney. The brace in the first position 122' is extended/rotated to the far right. When the brace 122" is folded in the second position 122", it rotates towards the anchor 410. In the third position 122''', the brace 122''' rotates to capture the frame 421 of the gurney. FIG. 4C shows the gurney frame 421 sandwiched between the brace 122''' and the plate element 412 of the anchor 410.

In the event of an emergency and immediate access to the patient is required, the apparatus 100 may be quickly pulled backwards and away from the patient/gurney 424 (e.g., at about a 15-degree angle), via the two L-shaped handles located on either side of the apparatus 100, thus allowing unrestricted access to the patient within seconds. This may be accomplished because the anchor plate 410 sits in between the gurney 424 or hospital mattress 422 and the frame of the bed/gurney, utilizing the weight of the patient's upper torso and head, to apply downward pressure on the anchor 410, sandwiching it between the mattress 422 and frame 421. The anchor plate 410 may also be lined with rubber silicone on the edge, to provide extra friction, preventing it from sliding around during transport.

This unique safety design of the anchor 410 and brace 122 together, allow for the security and stability of the apparatus 100 on the gurney 424, while also prioritizing the patient's safety in the event of an emergency.

Figure 5A:
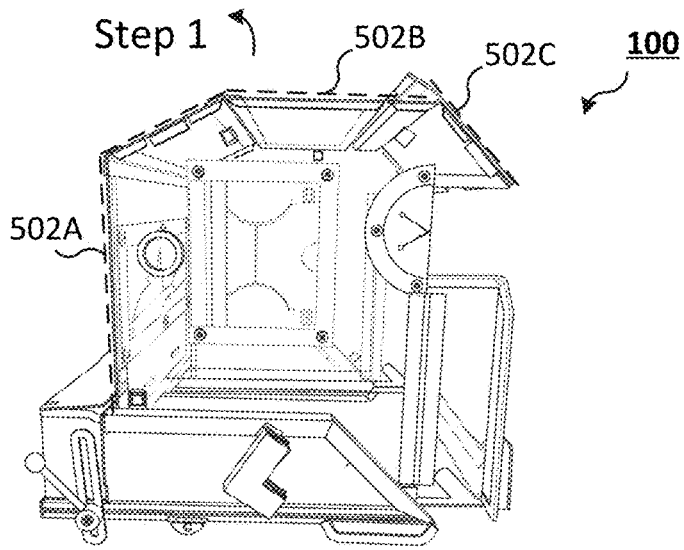
FIG. 5A is a side view of the exemplary apparatus showing steps to collapse the apparatus, according to an embodiment of the disclosure.
Figure 5B:
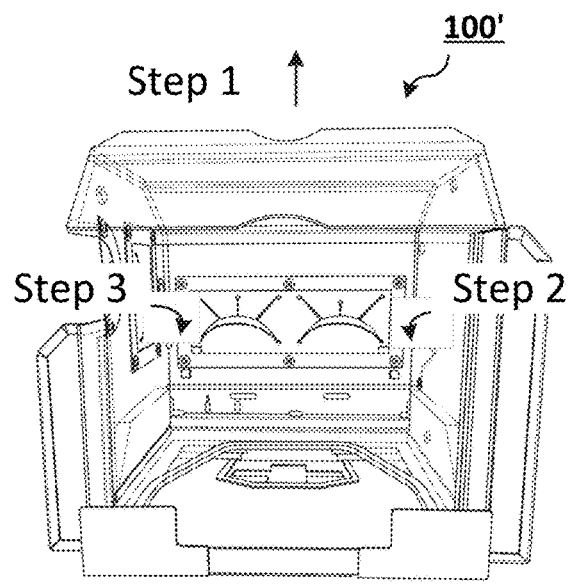
FIG. 5B is front view (from patient's perspective) of the exemplary apparatus showing steps to collapse the apparatus, according to an embodiment of the disclosure.
Figure 5C:
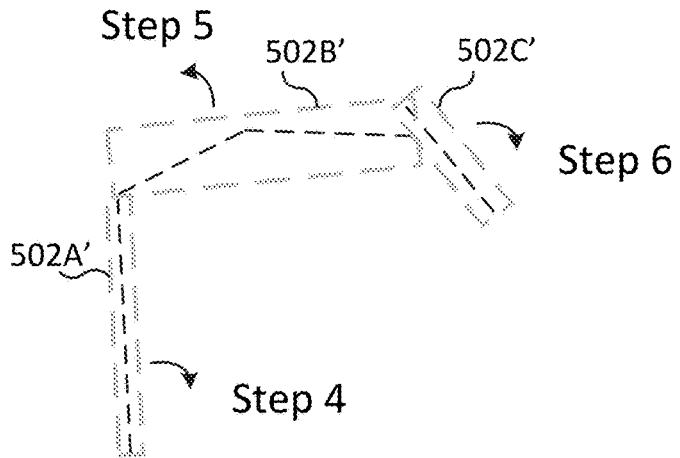
FIG. 5C is an illustration showing steps to collapse the apparatus, according to an embodiment of the disclosure.
Figure 5D:
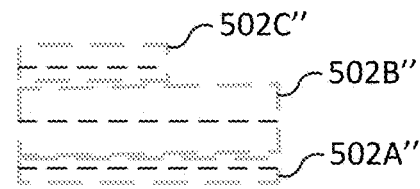
FIG. 5D is another illustration showing a representation of the collapsed state of the panel segments of the apparatus, according to an embodiment of the disclosure.

FIGS. 5A-D are views and illustrations showing steps to collapse the apparatus 100, according to an embodiment of the disclosure, with FIG. 5A showing is a side view of the exemplary apparatus 100, FIG. 5B showing a front view (from patient's perspective) of the exemplary apparatus 100', FIG. 5C showing an illustration of steps 4-6, and FIG. 5D showing a representation of the segments in the collapsed configuration. The panels of the apparatus 100 are hinged at various points of the panels. Some of the panels may be completely separate from other panels. For example, the top panel (e.g., 150 of FIG. 1) is not connected or hinged to the side panels and may be completely separated—"C" or "U" grooves and magnets may be used to couple these panels together.

In the sample of FIG. 5A, the panels are hinged at the edges of the dotted line representations; for example, segment 502A is hinged at the bottom and top of the dotted line representation. Segments 502B, 502C have multiple hinges anywhere the dotted line representation creates an angle. As illustrated, any of the panels may include multiple segments that are hinged together.

In the first step of FIG. 5A, the top 502B/502C and back 502A (which may form one contiguous piece) may be pulled up and rotated counterclockwise as illustrated by the 'Step 1' arrow. The same step 1 is illustrated in FIG. 5B showing the top/back panels being pulled up and away from the two side panels. The top/back panels may be mated to the side panels using various latching or alignment elements. For example, the panels may be joined together with any combination of tabs, neodymium magnets, velcro, latches, etc.; these various mating elements may need to be detached first before folding the panels out of the way so that each step may require multiple sub-steps. For example, in the embodiment of FIG. 5A, the top panel may have 'U' or 'C' shaped groove pieces to grab onto the thin edge of the side panels and the panels may include corresponding magnets to firmly mate together so that minor movement does not separate the panels. In such an example, step 1 may include detaching the magnets, pulling the panels away from the grooves and then pulling the top/back panel away from the side panels.

In step 2 and step 3, the side panels are folded in and down into the base. The side panels are not hinged or permanently connected to the top/back panel (e.g., 502A, 502B, 502C) so they may move freely and independently of the top/back panel. Each side panel may be hinged at the bottom/base of the respective panel so in step 2 the right panel may be rotated counter-clockwise to fold the panel down towards the base; in step 3 the left panel may be rotated clockwise to fold the panel down towards the base. The steps may be reversed as suitable based on user preference and design. For example, step 2 may include the left side being folded down before folding down the right side down as step 3.

Moving to FIG. 5C, the top and back panels may have multiple hinges. The hinge elements may be connected in any suitable fashion based on user preference and design. In the example of FIG. 5C, at step 4 the back panel 502A' is folded down (clockwise) and then at step 5 the top panel segment 502B' (which may include multiple hinged pieces) is rotated counter-clockwise to fold flat against the back panel 502A'. At step 6, the front/rear piece 502C' is folded clockwise to lay flat against 502B'. FIG. 5D is a representation of the panels folded and collapsed; the representation is exaggerated for illustrative purposes.

Folding the apparatus 100 out (e.g., deploying the apparatus 100 for use with a patient) may be the reverse process from step 6 to step 1. For example, the apparatus 100 may being with the panels folded as represented in FIG. 5D and the operator (or any other person/machine capable of handling the apparatus 100) unfolding from step to step 1.

While FIGS. 5A-D show one exemplary embodiment, those skilled in the art will readily recognize that various implementations may be possible. For example, the panels and components may be hinged at any suitable points; alternatively, or additionally, the panels and components may use mechanisms other than hinges to allow the panels and component to articular and move or fold relative to the apparatus 100. Any or all edges may be hinged or unhinged based on user preference and design.

Figure 6:
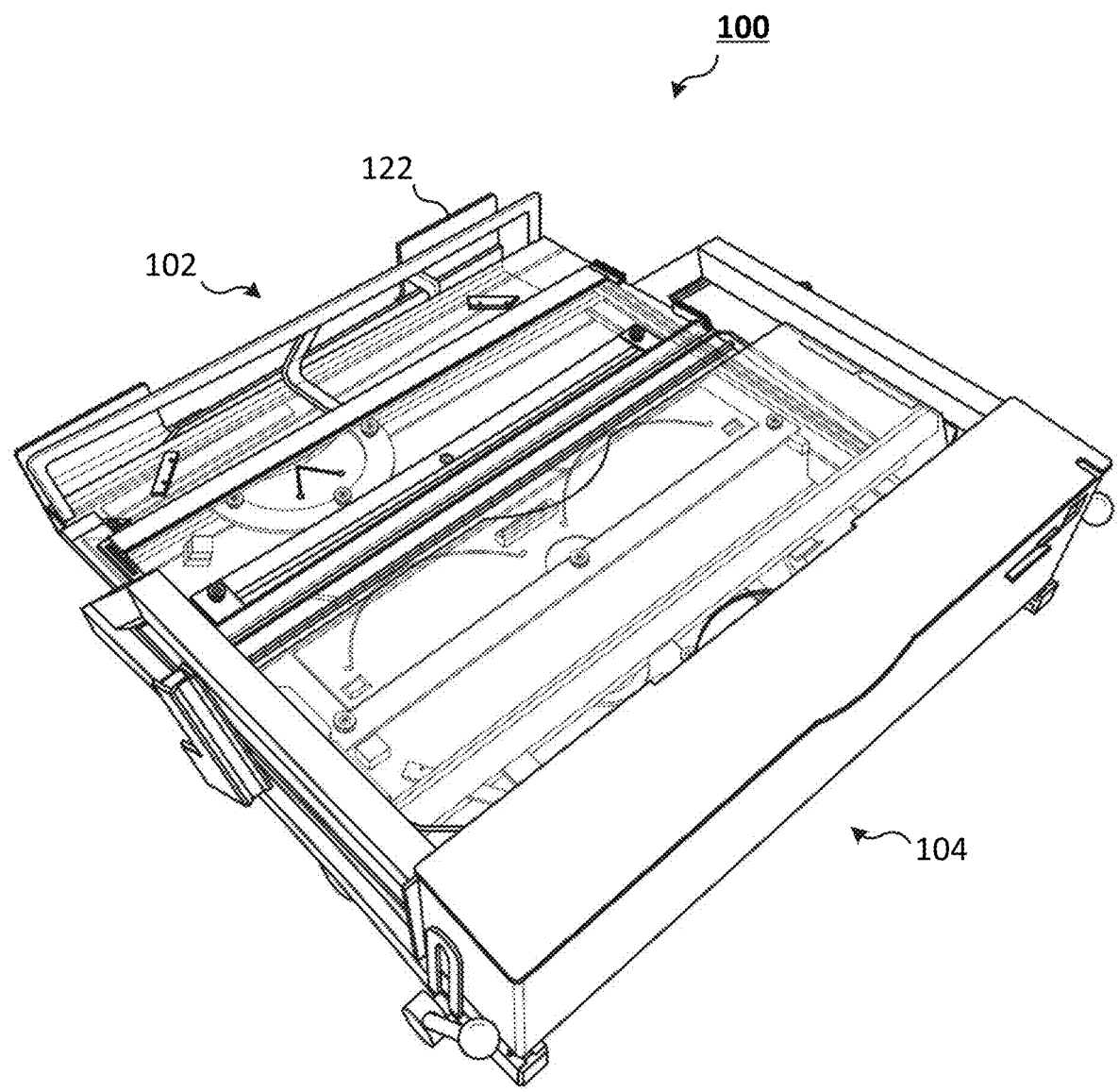
FIG. 6 is perspective view of the exemplary apparatus in a collapse state, according to an embodiment of the disclosure.

FIG. 6 is perspective view of the exemplary apparatus in a collapse state, according to an embodiment of the disclosure. The apparatus 100 in FIG. 6 is shown with the operator side 104 towards the bottom right of the figure and the patent side 102 shown toward the top left of the figure. The protective shield 122 is shown deployed in the example of FIG. 6.

Figure 7:
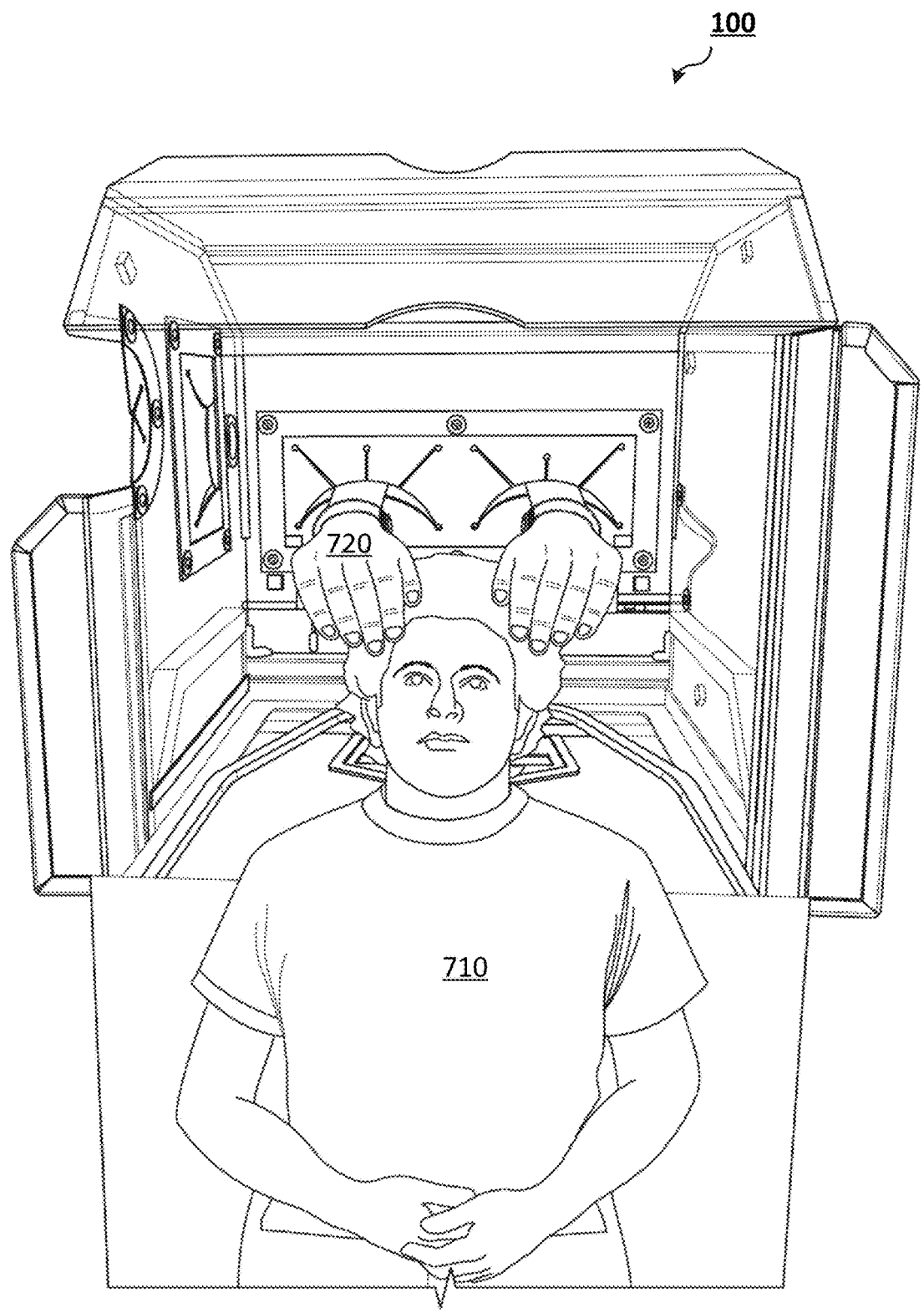
FIG. 7 is front view (from the patient's perspective) of the exemplary apparatus as used by an operator and patient of the apparatus, according to an embodiment of the disclosure.

FIG. 7 is front view (from the patient's perspective) of the exemplary apparatus as used by an operator and patient of the apparatus, according to an embodiment of the disclosure. FIG. 7 omits various features for simplicity and to avoid obscuring parts of the figure—some omitted features include various accessories including filters and motors, drapery over the patient. The patient 710 may be lying on a gurney or hospital bed (not shown) while receiving care from an operator 720. The various ports of the apparatus provide easy access for the operator and any assistants to access the patient. While FIG. 7 shows one configuration, the disclosure is not so limited. For example, as discussed above, the access ports may take any configuration including embodiments with integrated gloves on the access ports.

When the patient 710 is centered and positioned comfortably on a surface, e.g., a gurney, stretcher, operating room (OR) table, the operator 720 opens the apparatus 100 and carefully aligns it above the patient 710 while ensuring complete coverage of the patient's 710 head. There are two safety hooks located bilaterally on the operator 720 side of the apparatus, providing a gap (e.g., 1½"×⅜") for the operator 720 to secure the apparatus 100 down to the surface (e.g., gurney/stretcher) using the "rope" of their choice. In some embodiments, bungee cord may be used. The safety hooks hold the apparatus 100 down to the surface (e.g., gurney/stretcher) in the event of sudden jarring or accidental tipping of the surface (e.g., gurney or stretcher). The use of the safety hooks is required for use in the transportation setting due to the smaller stretcher width (e.g., 24") and the greater risk of tipping the apparatus 100 over during the transportation process.

Once the apparatus 100 is properly positioned, an assistant may place clear vinyl drape (e.g., 96"×36") over the patient's 710 thoracic/abdominal region while aligning the marked alignment elements (not shown) of the apparatus with the target corners on both sides of the front lid of the apparatus 100. The operator 720 must ensure that the drape is centered and wraps completely over the top of the lid in order to form a "pseudo" seal, by creating a physical obstacle for ascending aerosolized droplets. The assistant then hands the left corner of the drape to the operator 720, where the operator 720 pulls the drape taut and slides it in between the gap of the protruding L-shaped tension lock and the mattress of the surface (e.g., gurney/stretcher), creating the tension for the 2-part locking system. The action is followed through by pulling the drape thru a ⅛" gap located on the medial side of the left L-shaped handle. This system creates sufficient tension to lock the drape in place, while the apparatus 100 is in use. The same steps may be repeated for the right side.

Some embodiments may provide for ample interior room. The interior dimensions of the apparatus may be configured to provide the ample space; in some examples the apparatus may measure up to 21.44"×21.88"×21.63" (l×w×h) or larger, which may provide ample room for an operator to freely maneuver medical instruments inside, such as a bougee or stylet without issue.

Some embodiments may include bilateral tension locks/handles. There may be two L-shaped handles strategically located on both sides of the base. These may be lined with closed cell silicone foam on the inside/edges, allowing the operator to easily slide in and secure the drape. After the drape is folded over the top of the rear panel and folded upon itself over the corners of the rear panel, the remaining length of the drape may be pulled taut and slid in between the silicone foam on both sides. This tightly secures the drape by pinching it between the two layers of closed cell silicone foam, utilizing these bilateral tension points as anchors and the corners of the rear panel as the fulcrum. By using tension to secure the position of the drape, instead of adhesives, buttons, clamping, etc., this allows for additional safety for the patient in the event of an emergency. If only the drape needed to be removed for immediate access to the patient, the drape may be quickly pulled up and forward from the top center section, right above the rear panel. The weight of the apparatus would resist the force of the drape being pulled away and the drape would slide out from between the silicone foam. By not securing the drape using adhesives, clamps, buttons, etc., the drape won't snag on the apparatus as it is being pulled away, which could jar the patient during the process. Additionally, the anchor and brace would also act as a secondary safety net, ensuring that the entire unit does not get lifted up when the drape is removed, potentially injuring the patient.

The placement of the handles may allow the operator to properly adjust the positioning of the apparatus once it is placed on the gurney, as well as allow the operator to quickly pull the apparatus back and away from the patient and gurney, in the event of any emergency. They may also allow for easy transporting/relocating of the apparatus while it is fully assembled.

Some embodiments may include bilateral safety mounts. Found towards the patient side, and on both sides of the base may be two gurney mounts which hug the gurney mattress from both sides, keeping the apparatus aligned with the mattress and preventing the apparatus from sliding left to right (side to side) during transport or if the apparatus is accidentally jarred during use. These mounts are lined with silicone rubber to provide additional friction against the cloth material on the mattress, decreasing any unwanted movement of the unit.

Some embodiments may include bilateral locks. The mechanism that attaches the anchor and brace system to the base is adjusted and locked by bilateral handles which ensure that the distance between the bottom of the base and the anchor plate remain the same at all times. Adjusting the bilateral locks may allow the operator to compensate for the different thicknesses found in a variety of gurney/hospital bed mattresses that the apparatus may be installed on. This adjustment may allow the apparatus to be installed on a wide variety of mattresses in the outpatient and inpatient setting. Most standard gurneys may have a two-inch-thick mattress, while most hospital beds may have a six inch thick mattress, both of which may easily be accommodated. The embodiments are flexible and may accommodate gurneys, beds, and other body support systems of any size according to preference and design requirements.

Some embodiments may include a central safety catch, including a 2"×8"×⅛" aluminum lip that may extend downward from the base's frame and catch onto the head of the mattress. This may prevent the apparatus from moving forward when the head of the gurney or hospital bed is elevated, allowing the patient to sit upright and breathe more comfortably while maintaining enclosure integrity.

Some embodiments may include a storage box at the front of the base. The storage box may include specifically designed mounts for storage of a motor, battery, filters, and IV pole. The apparatus may have specifically designed slots that anchor the IV pole in a stored position, when not in use, as well as slots for an upright mount of the IV pole when the apparatus is fully deployed and an IV bag is attached. The lid of the box may have a 3/16" deep by 8" wide slot towards the rear, which may allow for two collapsed apparatuses to be stacked on top of each other securely. The slot accommodates the central safety catch (discussed above) that protrudes downward from another apparatus, securely keeping the two collapsed apparatuses together, preventing them from slipping off of one another when stored away on a shelf.

Some embodiments may include a handle, including a 6" wide handle, located on the operator side of the apparatus, at the bottom of the front of the storage box, allowing for easy carrying of the apparatus when it is fully collapsed. The handle may be attached to the frame of the entire unit, giving the user a sturdy and well-balanced position to hold the apparatus from.

In some embodiments, clear vinyl drape may be used as cover for the apparatus. In other embodiments, painters cover may be used in the event that the original drape is damaged or dirty. Once the clear drape is secured in place, the operator of the apparatus may proceed to intubate the patient if that is the next step. The front panel of the apparatus has a horizontal flip up access door (e.g., measuring 6"×18" to provide suitable access) and when opened fully (e.g., 180 deg), can be held open by making contact with the magnet above it (e.g., 3" in some embodiments). This rectangular access door allows the physician/paramedic to reach their arm inside the apparatus and comfortably intubate the patient while protected behind the clear acrylic. The access door (e.g., 6"×18") has two layers of clear vinyl on the inside of the apparatus. The first layer is precut with two horizontal cross-shaped patterns, measuring, e.g., 6" apart. The second layer of vinyl measures, e.g., 11"×20" and acts as a secondary barrier to help reduce the amount of aerosolized droplet particles that may travel/escape through the two arm openings in the first layer of clear vinyl, that is being used by the physician/paramedic during the procedure. The wide horizontal opening allows for much improved lateral mobility of the physician's or paramedic's forearms during the intubation or extubation procedure. With every physician and paramedic unique and different, the horizontal opening enables the operator to more naturally and comfortably perform the intubation procedure, leading to a safer, and more successful outcome. The ease of use that comes with the increased lateral mobility provides the physician with increased maneuverability of their tools, and increased range of motion (ROM) in their forearms and wrists.

The smaller top panel is angled at, e.g., 26 degrees to reduce the amount of glare from light directly above, increasing the operator's visual field. The angled panel also serves to promote air circulation within the apparatus, towards the suction vent located at the top of the back panel, by decreasing the amount of stagnant air that accumulates in the corners of the apparatus. The larger top panel is a flat surface measuring, e.g., 11"×22" that doubles as a workspace area, if items need to be placed there for upcoming use.

There is a 2" acrylic lip that extends perpendicularly on the end of both of the side panels. This lip is 2" extension beyond the "soft" width, that is one piece and bent 90 deg, thermoformed. This 2" lip functions as an aerosol deflector and prevents the free-flow movement of any infectious aerosolized particles from escaping the containment field, which is the area contained within the apparatus and clear vinyl drape. The 2" lip physically prevents the accidental spread of infectious aerosolized droplets from travelling freely between the two side panels of the apparatus. The 2" lips that extend also serve as the front stabilizers of the apparatus, by creating a wider base footprint on the gurney and increasing the safety and security of the apparatus.

The back panel may be angled, e.g., at 45 degrees to increase the volume of air exposed to the suction port when in use. The suction port is directed towards the general area of the patient's mouth and nose, to increase the chances of sucking up and filtering the expelled respiratory droplets.

To accommodate multiple patient sizes, the left and right panels in the "soft" width region may flex outward to accommodate patients with wider shoulders. The hinges on these panels may be spring loaded and return the panel back to its original position when the apparatus is removed.

The apparatus may be compatible with most standard gurneys/stretchers 24" and above, owing to its compact, yet versatile size.

The apparatus may fold down to a height of only, e.g., 5½", allowing it to be easily transported or stored away until needed. Due to its compact size, the apparatus may be taken into the field and setup by paramedics and emergency medical technician (EMTs) after they make the initial contact with the potentially infected patient. When the patient is transported from the ambulance into the emergency department (ED), the apparatus contains and isolates the patients' airborne respiratory droplets, thereby minimizing the risk of exposure to numerous healthcare professionals. Once the patient is admitted, the apparatus can be swapped out to the one the hospital uses, if they have their own, or the paramedics can set up an exchange plan with their local hospitals, to further minimize exposure during transfer of the apparatus.

In some embodiments, the self-contained apparatus may collapse to a height of only, e.g., 5½" and expands to a height of approximate 22" when in use. The apparatus may maintain a base footprint of about 23"×23". When multiple apparatuses are stored in their collapsed state, the apparatuses may interlock when folded and stacked upon one another, allowing for better organization.

The triangular shaped base corners of the apparatus may aid with the overall stability of the structure of the apparatus, while also creating a bottom cover for the trimmed corners of the stretchers/gurneys, which would otherwise be left open. The baseboard corners in the apparatus may allow the apparatus and the patient to be closer to the operator of the apparatus, leading to an improved field of vision of the patient's airways. This also allows the operator to maintain better ergonomics, reducing neck and back strain from reaching forward and hunched over.

Some embodiments may include two safety catches located at the bottom of the front of the operator panel designed to prevent the apparatus from sliding down the gurney/stretcher mattress when the head of the gurney/stretcher is elevated. The safety catch may also accommodate gurneys/ambulance cots with mattress head widths narrower than 8", allowing the narrower mattresses to slide in between the safety catches, preventing the apparatus from sliding down into the patient when the head of the gurney/stretcher is elevated.

Figure 8:
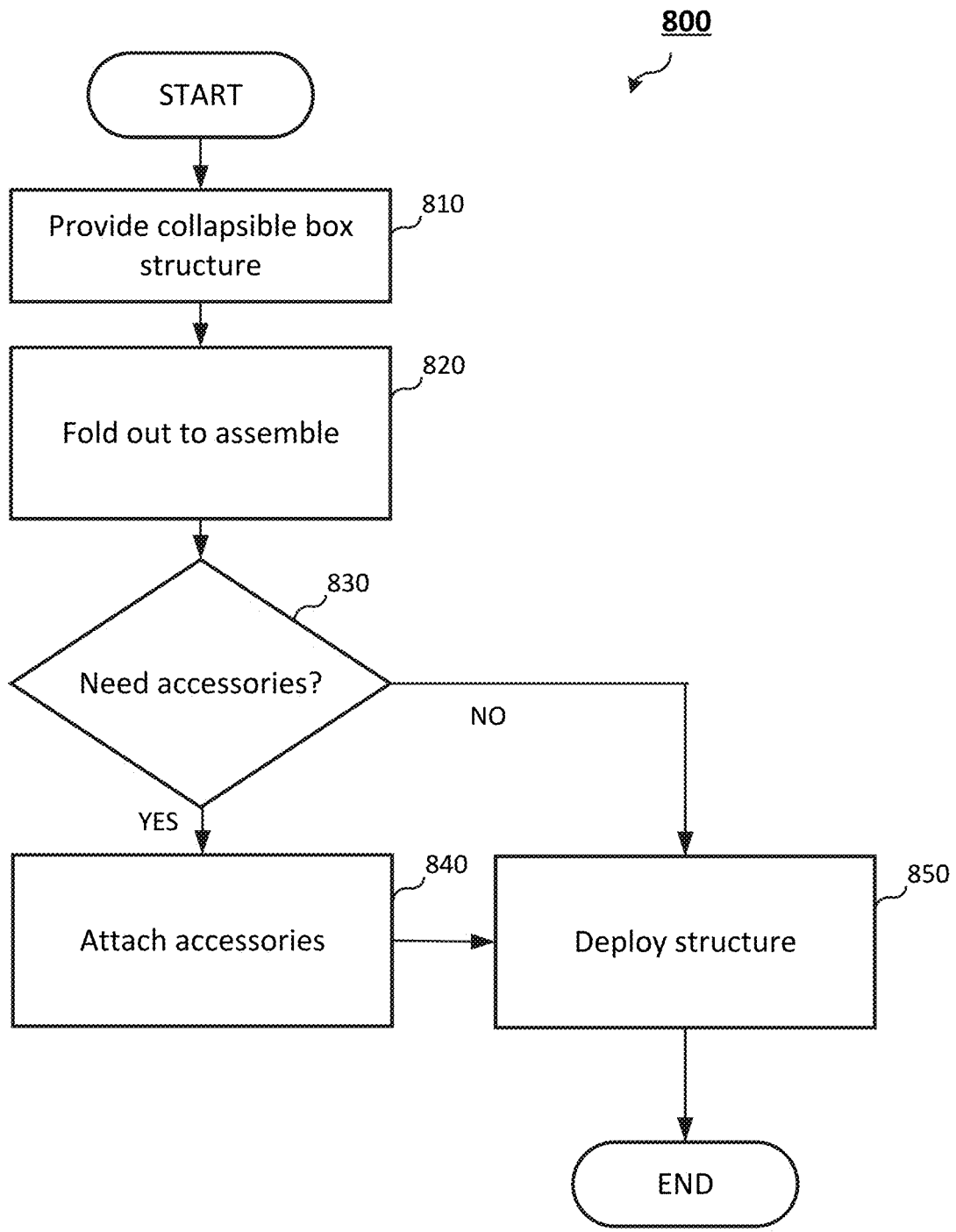
FIG. 8 is an exemplary flow diagram illustrating methods for assembling the exemplary portable collapsible air isolation apparatus. The apparatus may be the apparatus 100 of FIG. 1.

FIG. 8 is an exemplary flow diagram illustrating methods for assembling the exemplary portable collapsible air isolation apparatus. The apparatus may be the apparatus 100 of FIG. 1. The method may be performed by an operator, an assistant, or any person capable of handling the apparatus. In some embodiments, an automated attendant, a machine, a robot, etc. may perform any or all of the steps of FIG. 8. The person or automated entity performing the steps may be called the "assembler."

The method may include, at step 810 providing a collapsible box structure. The collapsible box structure may be the apparatus 100 of FIG. 1. In some examples, the structure may be partially assembled with all hinges installed such that only folding/folding and minor steps such as aligning mating points are needed. In some examples, the structure may be provided in any unassembled form including completely unassembled (hinges not screwed, no items fastened, etc.) as a kit. In the examples where the structure is partially or entirely unassembled (e.g., provided as a kit), the assembler may perform additional steps (e.g., screwing in attachments/accessories, joining various elements, etc.). In some examples, the structure may have been previously used and folded for storage.

The method may include, at step 820 folding out the structure to assemble the structure for use with a patient. Step 820 may be represented by the reverse process of FIGS. 5D-A with the structure beginning in the folded state (e.g., FIG. 6 and FIG. 5D) and proceeding backwards from step 6 to step 1.

The method may include, at step 830 determining whether accessories are needed for the apparatus 100. Some of the accessories may include drapery, a motor, filter, IV pole (for hanging an IV bag), etc. If any accessories are needed, the method may proceed to step 840. If no accessories are needed, the method may proceed to step 850.

The method may include, at step 840, attaching accessories to the apparatus 100. Some of the accessories may include drapery, a motor, filter, IV pole (for hanging an IV bag), etc. In the case of the IV pole, some embodiments of the IV pole may be attached as illustrated in FIG. 2, e.g., by using the hook and slot system. Drapery may be placed on apparatus 100 to cover any or all portions of the apparatus 100 including over the patient areas.

The method may include, at step 850, deploying the structure. Deployment may include using the structure in any of the suitable medical or other settings including on a gurney, hospital, other medical facility, etc. In the case of use on a gurney, the structure may be secured onto the gurney, e.g., as provided in FIGS. 4A-C and the associated description. A patient may be placed inside the structure, e.g., as provided in FIG. 7 and the associated description.

In some embodiments, optional steps during or after step 850 may include providing a patient for the structure, and positioning or placing the patient within the structure.

Figure 9:
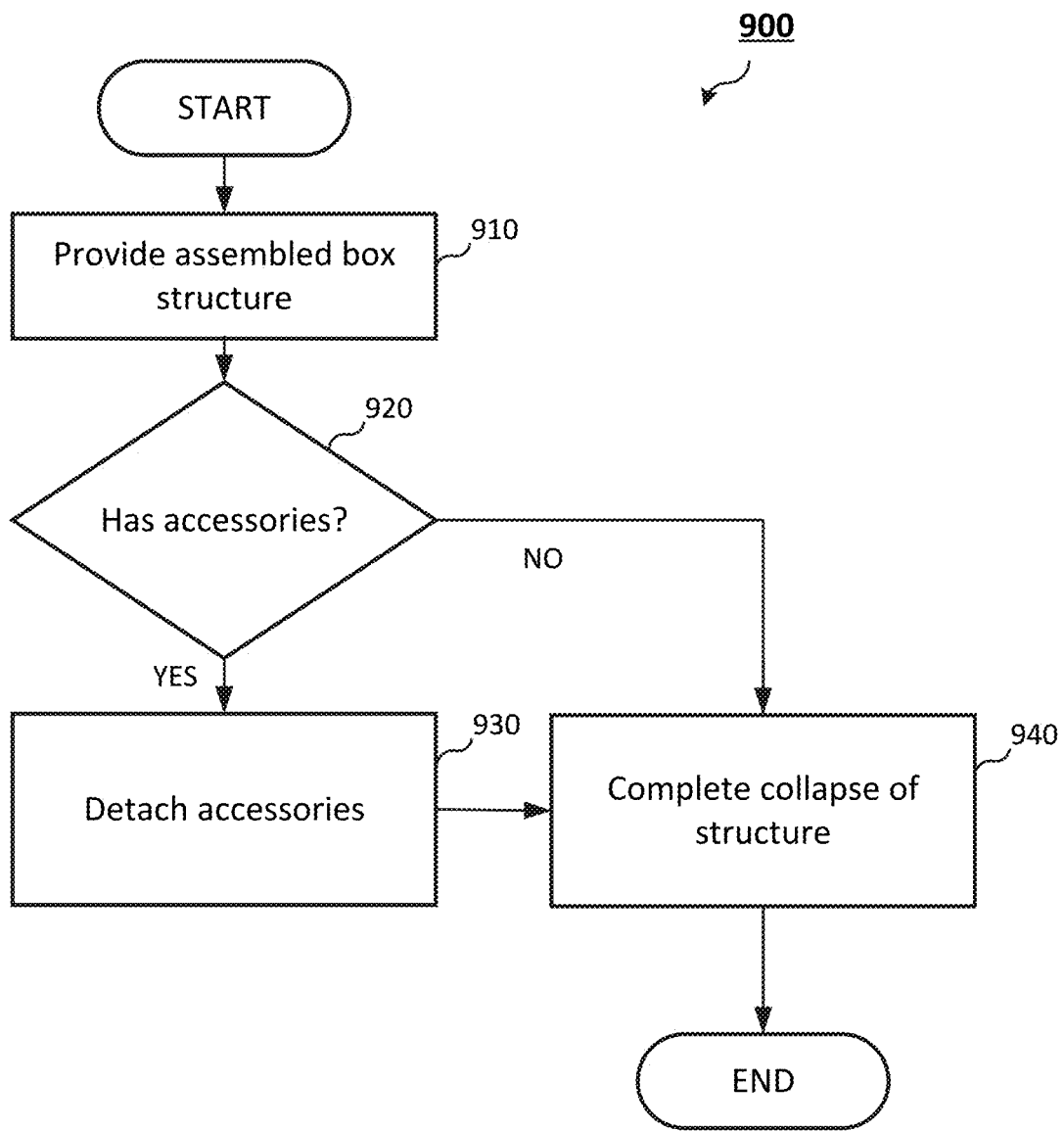
FIG. 9 is an another exemplary flow diagram illustrating methods for disassembling or collapsing the exemplary portable collapsible air isolation apparatus. The apparatus may be the apparatus 100 of FIG. 1.

FIG. 9 is another exemplary flow diagram illustrating methods for disassembling the exemplary portable collapsible air isolation apparatus. The apparatus may be the apparatus 100 of FIG. 1. The method may be performed by an operator, an assistant, or any person capable of handling the apparatus. In some embodiments, an automated attendant, a machine, a robot, etc. may perform any or all of the steps of FIG. 9. The person or automated entity performing the steps may be called the "disassembler."

The method may include, at step 910 providing an assembled collapsible box structure. The collapsible box structure may be the apparatus 100 of FIG. 1. In some examples, the assembled structure may have been deployed, e.g., for use with a patient undergoing medical treatment. In some examples, assembled structure may have been deployed, e.g., for use with a gurney or medical bed, etc. In some embodiments, optional steps during or before step 910 may include removing a patient from the structure, and/or detaching the structure from frame(s) such as a gurney, bed, mattress, etc.

The method may include, at step 920 the method may determine whether the structure has accessories. If the structure has accessories, the method may proceed to step 930. If the structure does not have accessories, the method may proceed to step 940.

The method may include, at step 930, detaching accessories from the structure. Some of the accessories may include drapery, a motor, filter, IV pole (for hanging an IV bag), etc. In the case of the IV pole, some embodiments of the IV pole may be detached as illustrated in FIG. 2, e.g., by using the hook and slot system. Drapery may be removed from the structure that was used to cover any or all portions of the structure including over the patient areas.

The method may include, at step 940 collapsing or folding down the structure to disassemble the structure, e.g., for storage, transportation, to reduce the footprint, etc. Step 940 may be represented by the process of FIGS. 5A-D with the structure beginning in the deployed state (e.g., FIG. 5A) and proceeding from step 1 to step 6. In some embodiments, step 940 may include using a protective shield (e.g., 122 of FIG. 1); for example, the L-shaped protective shield may be flipped forward into position (as shown in FIG. 1) to protect the underside of the structure and its flex panel deflectors.

In some embodiments, optional steps (e.g., during or after step 940) may include stacking the structures together, e.g., for storage, transportation, or to conserve space, etc.

It is understood that the specific order or hierarchy of steps in the processes disclosed is an illustration of exemplary approaches. Based upon design preferences, it is understood that the specific order or hierarchy of steps in the processes may be rearranged. Further, some steps may be combined or omitted. The accompanying method claims present elements of the various steps in a sample order, and are not meant to be limited to the specific order or hierarchy presented.

Figure 10:
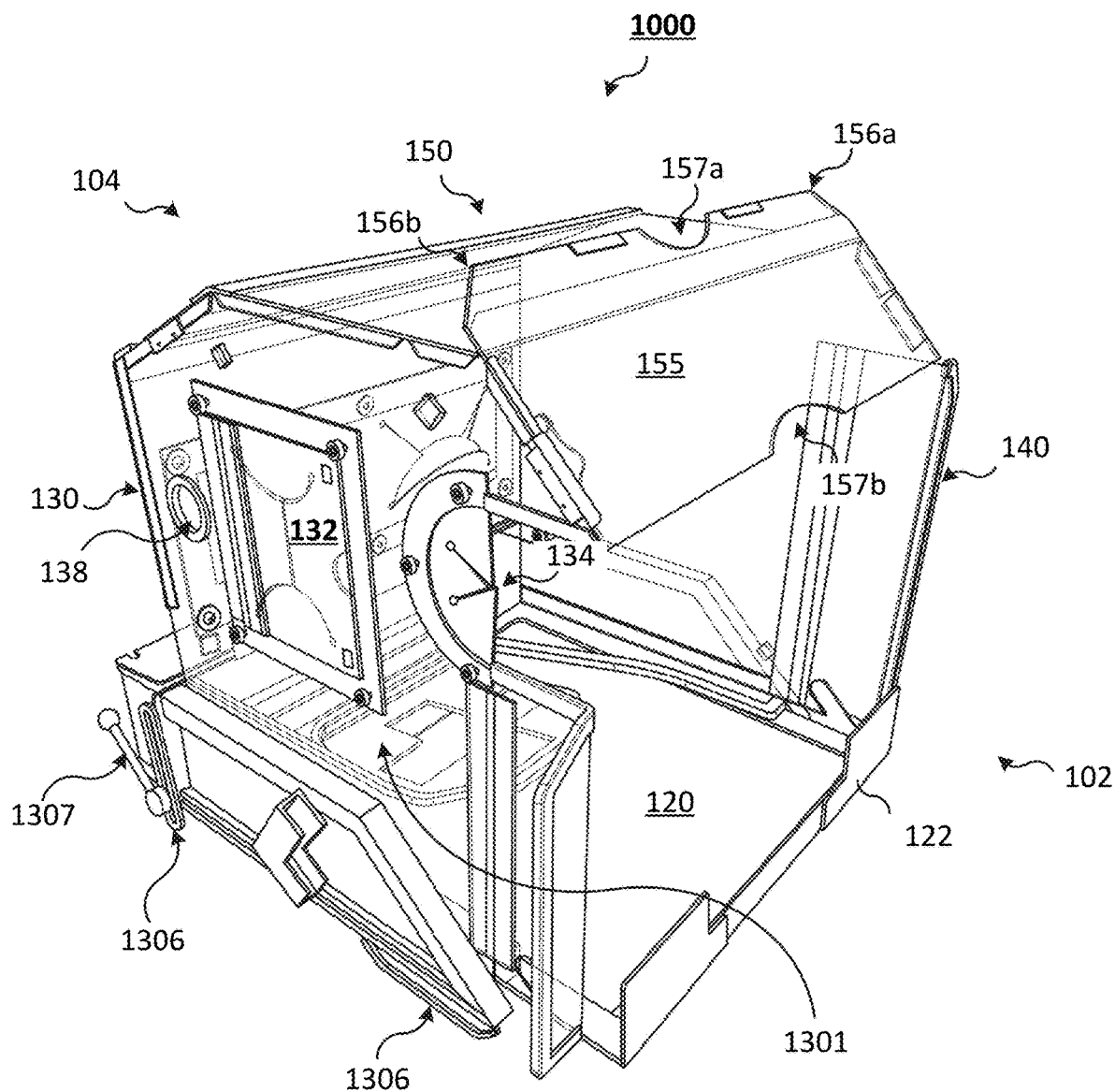
FIG. 10 is an alternative embodiment of FIG. 1 showing a perspective view of an exemplary portable collapsible air isolation apparatus for treatment of patients with respiratory symptoms, according to an embodiment of the disclosure.

FIG. 10 is an alternative embodiment 1000 of FIG. 1 showing a perspective view of an exemplary portable collapsible air isolation apparatus for treatment of patients with respiratory symptoms, according to an embodiment of the disclosure.

Figure 11:
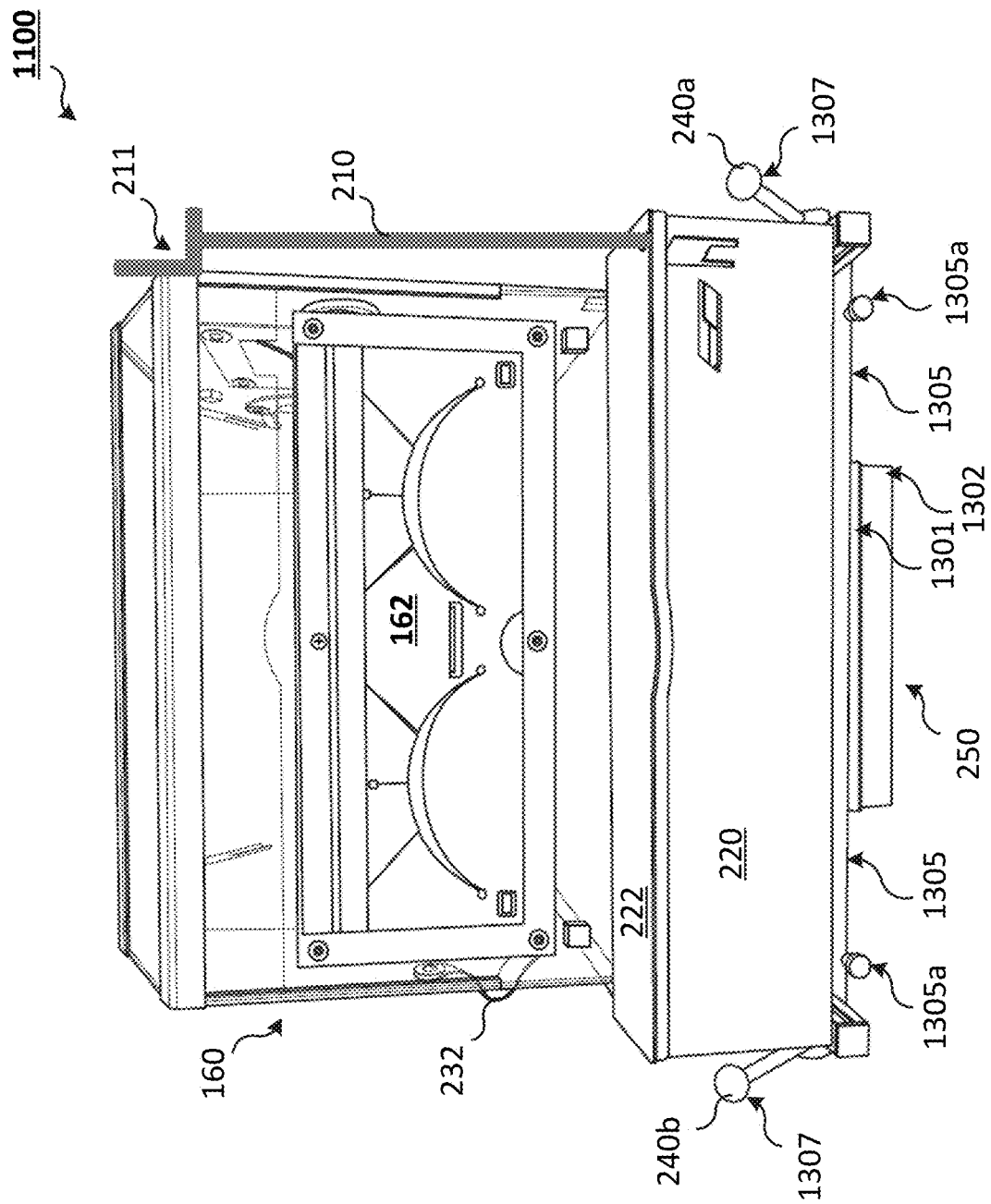
FIG. 11 is an alternative embodiment of FIG. 2 showing a view of the exemplary apparatus as viewed from the operator's perspective, according to an embodiment of the disclosure.
Figure 12:
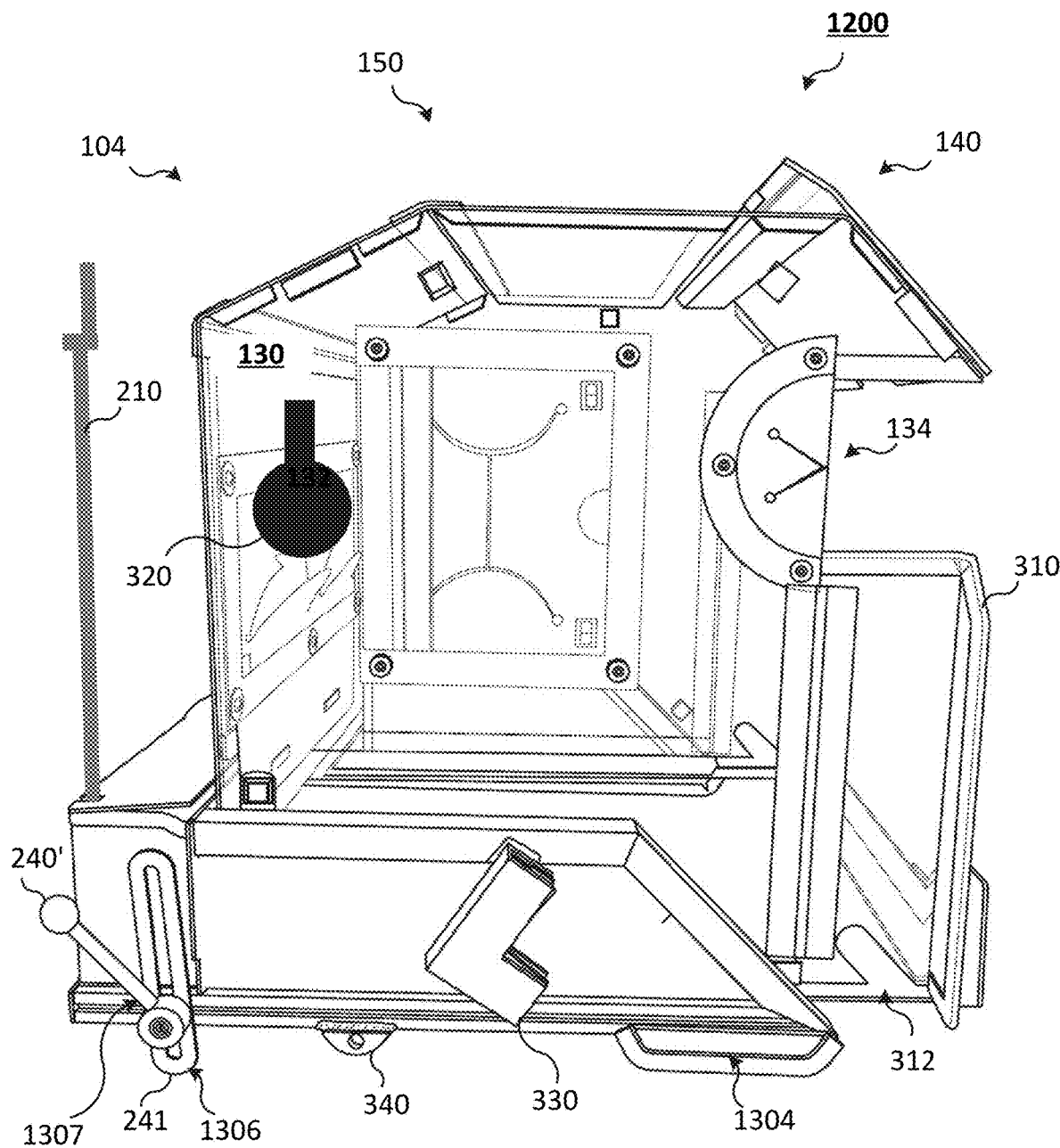
FIG. 12 is an alternative embodiment of FIG. 3 showing a side view of the exemplary apparatus, according to an embodiment of the disclosure.
Figure 13A:
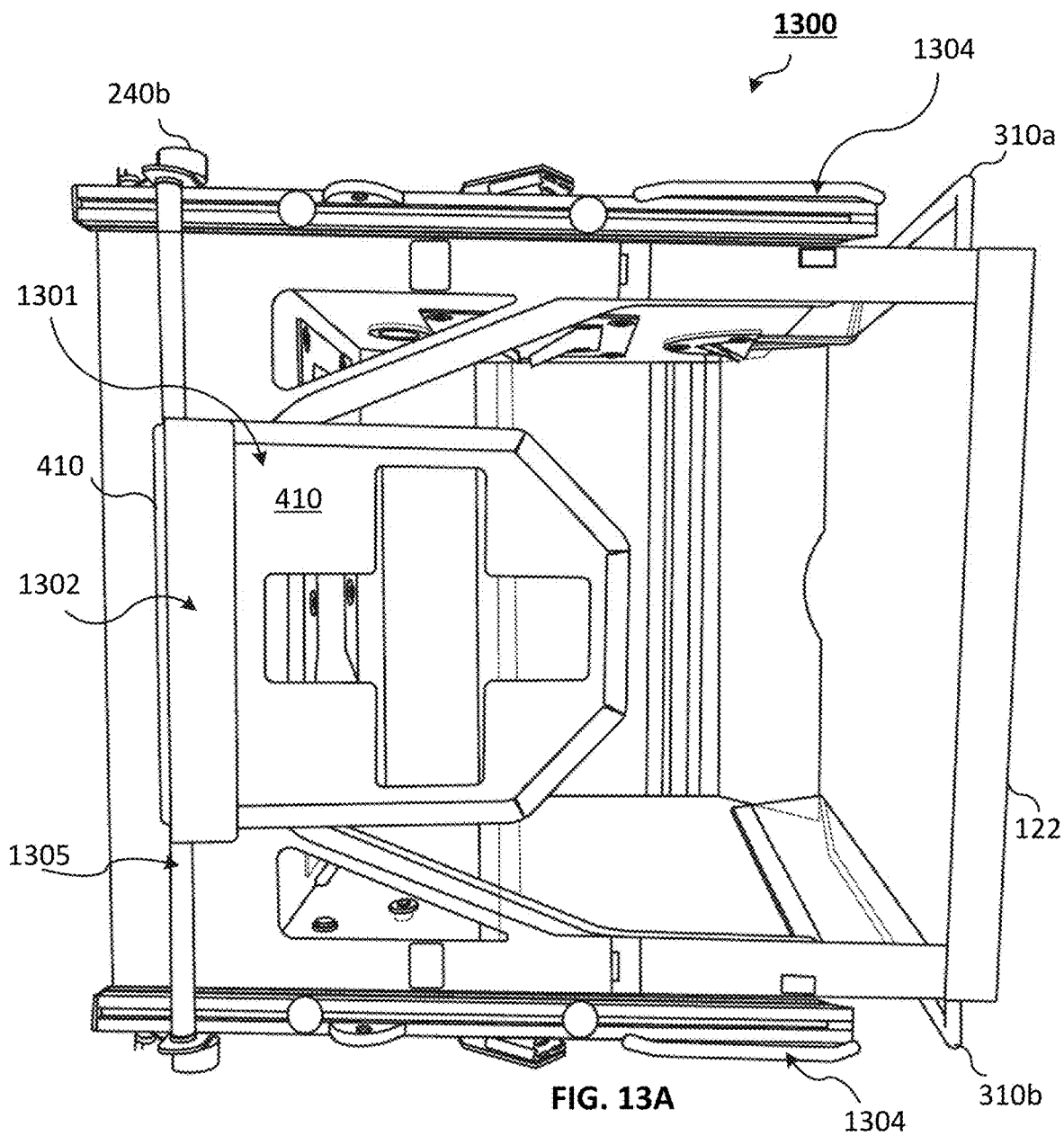
FIG. 13A is an alternative embodiment of FIG. 4A showing a bottom view of the exemplary apparatus, according to an embodiment of the disclosure.
Figure 13B:
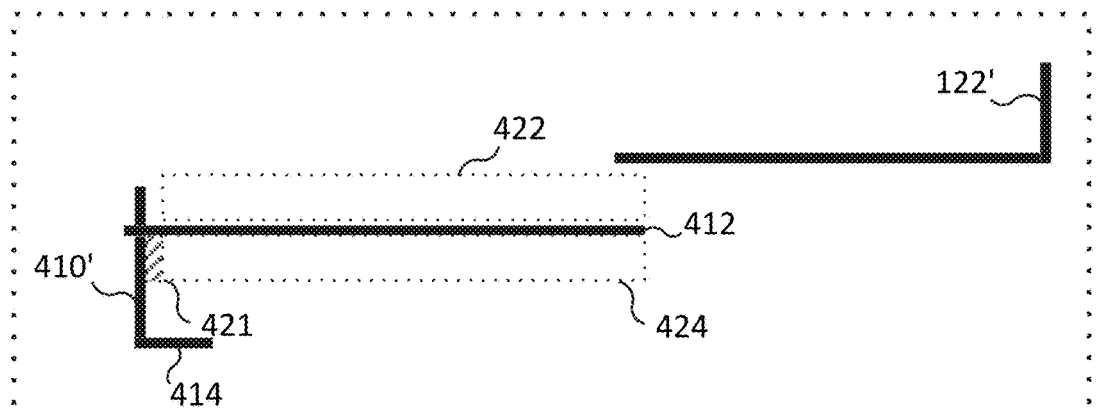

FIG. 11 is an alternative embodiment of FIG. 2 showing a view of the exemplary apparatus as viewed from the operator's perspective, according to an embodiment of the disclosure. FIG. 12 is an alternative embodiment 1200 of FIG. 3 showing a side view of the exemplary apparatus, according to an embodiment of the disclosure. FIG. 13A is an alternative embodiment of FIG. 4A showing a bottom view of the exemplary apparatus, according to an embodiment of the disclosure.

Figure 14:
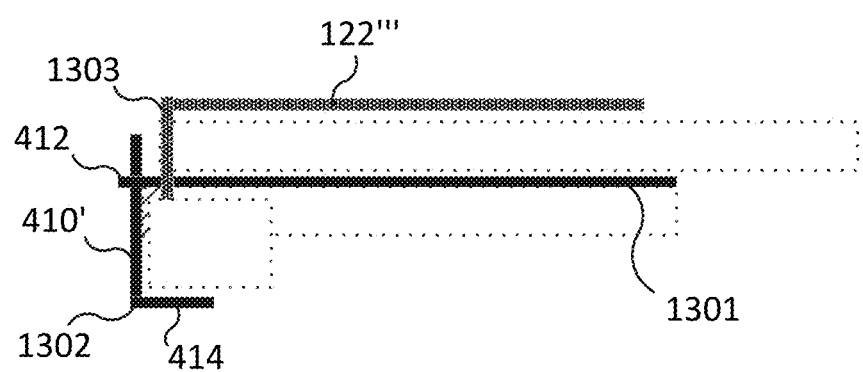
FIG. 14 is an alternative embodiment of FIG. 4C showing another side profile illustration with FIG. 4C showing rotation of the brace component, according to an embodiment of the disclosure.
Figure 15:
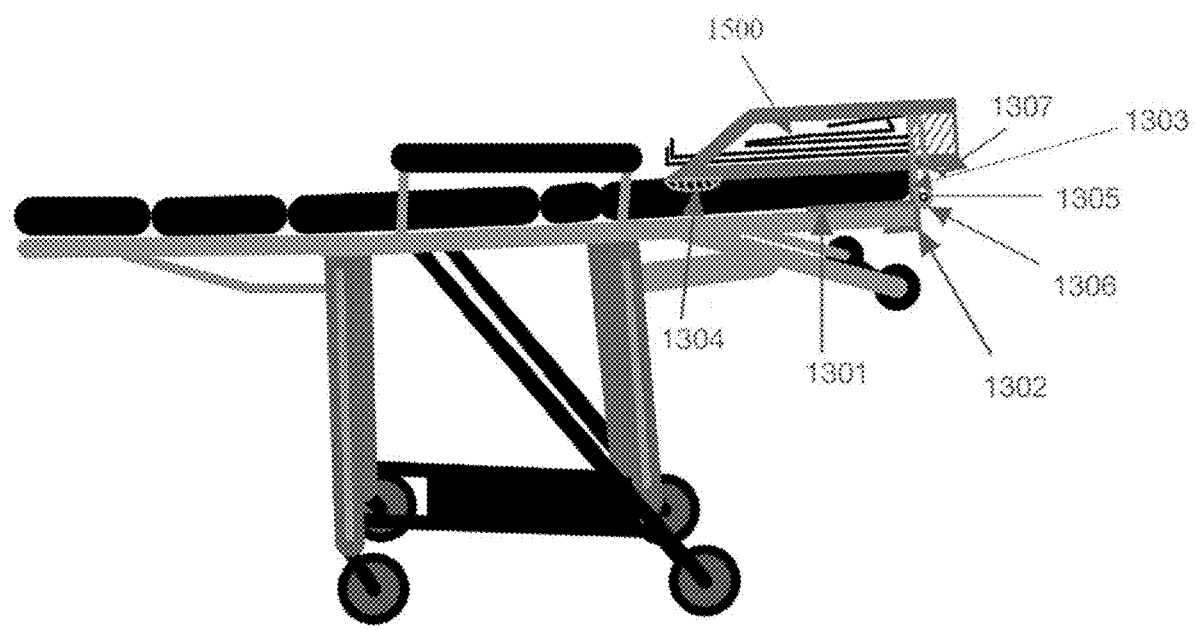
FIG. 15 shows a side view of the apparatus including the Bianca Box.
Figure 16:
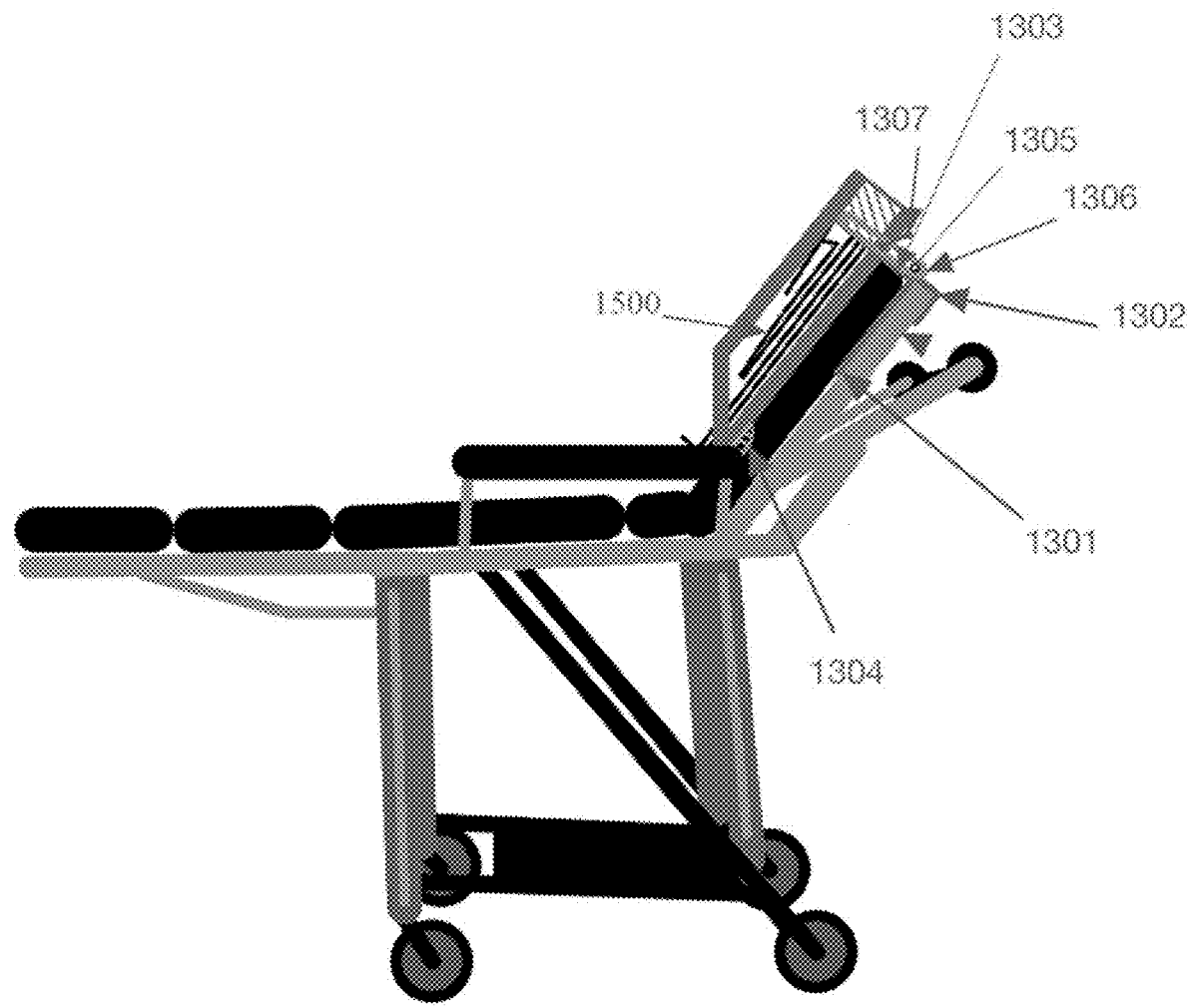
FIG. 16 shows a side view of the apparatus including the Bianca Box in another configuration.
Figure 17:
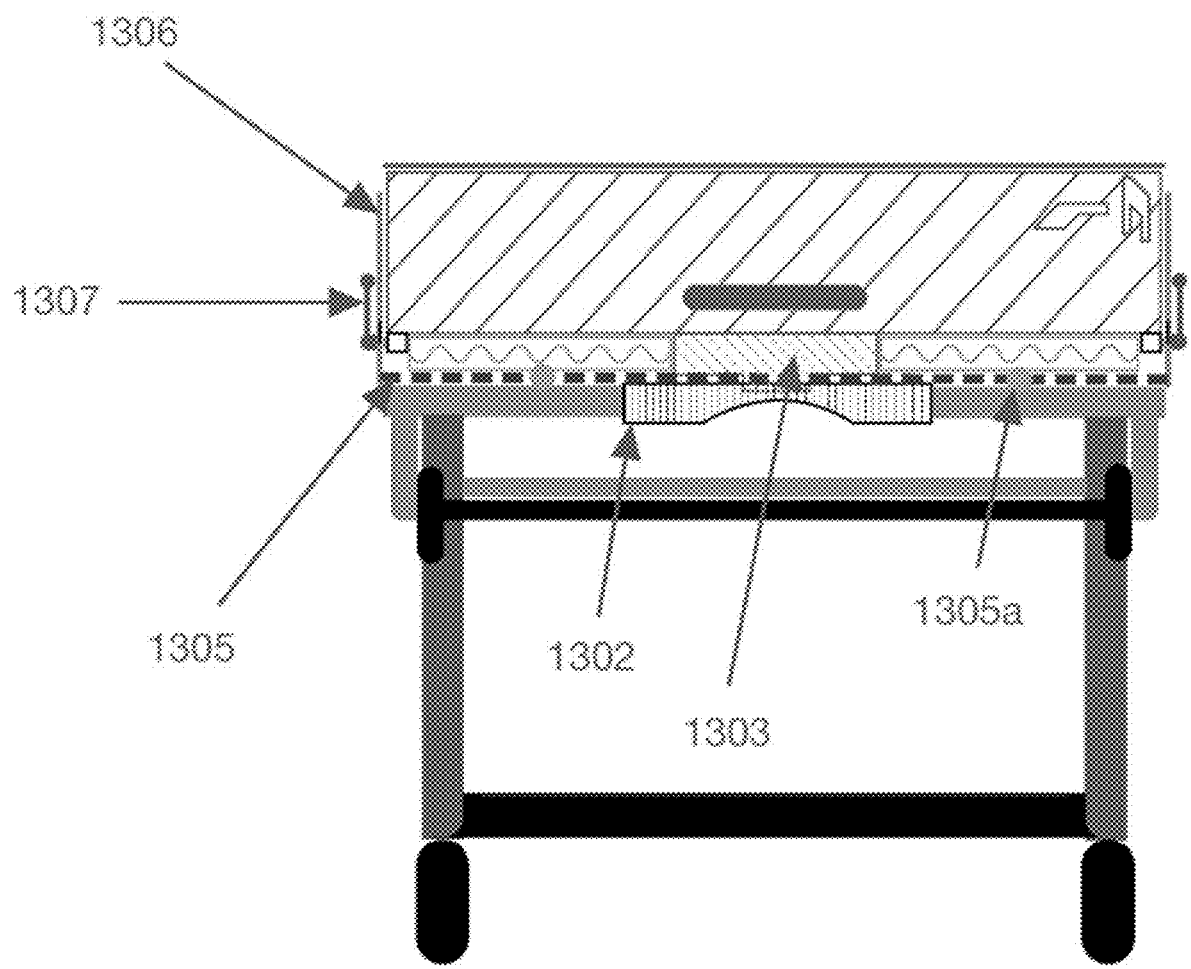
FIG. 17 shows another view of the apparatus including the Bianca Box.

FIG. 14 is an alternative embodiment of FIG. 4C showing another side profile illustration showing rotation of the brace component, according to an embodiment of the disclosure. FIG. 15 shows a side view of the apparatus including the Bianca Box 1500. FIG. 16 shows a side view of the apparatus including the Bianca Box 1500 in another configuration. FIG. 17 shows another view of the apparatus including the Bianca Box.

In FIGS. 10-14, similar components are labeled with the same numbers as those found in FIGS. 1-4C. The descriptions of the same numbers are omitted for brevity.

The apparatus which may be called a BIANCA Box may be comprised of (7) polycarbonate panels which are assembled to construct the isolation & containment structure with accompanying plastic drape. The base which may be called a BIANCA Base may include an aluminum base frame (with corresponding 3M® storage box) which provides rigidity and structural support for the attached BIANCA Box. BIANCA Box and Base together may be called the BIANCA Box unit. The BIANCA Anchor plate (anchor plate) 1301 may be a flat metal plate that is wedged in between the gurney or hospital bed mattress and its corresponding frame. The BIANCA brace (brace) 1302 may be an L-shaped metal plate with minimum inside height of one and a half inches, that interlocks with the BIANCA Anchor to be welded together. The BIANCA Box may include the BIANCA Anchor and Brace 1301, 1302.

In the above embodiments of FIGS. 10-14, the apparatus may include a fastening system or a mounting system. This system may be called a Universal Gurney Fastening System (UGFS). The UGFS may be is comprised of:
1. BIANCA Anchor plate
2. BIANCA Brace
3. Center safety catch (backing plate extension from BIANCA Base that interlocks with the BIANCA Anchor)
4. (2) Safety skid plates (attached to BIANCA Base)
5. Tubular pivoting crossbar with two locking thumb screws
6. (2) Slotted adjustable tension plates
7. (2) Locking Tension knobs The Universal Gurney Fastening System (UGFS) may be designed to attach and stabilize the BIANCA Box or any other apparatus, in some embodiments non-permanently, and in some embodiments without a closed loop fastening style, to a gurney (e.g. stretcher, hospital bed, surgical bed, ambulance cot, or similar 4 wheeled device with a mattress and frame) with or without the presence of a patient being transported. The UGFS may be primarily composed of two main components, the BIANCA Anchor and the BIANCA Brace. Together, they allow the entire BIANCA Box unit to be quickly and securely attached to any ambulance cot, gurney, stretcher, surgical bed, or hospital bed, with a 2"-6" (length of adjustable tension bars can be modified according to different thickness requirements) mattress height.

This unique system may allow for safe use of the BIANCA Box unit in multiple situations including, during emergency medical transport in the back of an ambulance, helicopter, plane, or boat, during maneuvering of a hospital bed/gurney, and while the bed is stationary. It keeps the BIANCA Box unit stable and prevents it from falling over during vehicle maneuvers, as well as during transport of a patient into and out of the ambulance or any other mode of transportation such as a plane, helicopter, or boat.

The UGFS prevents the BIANCA Box unit or other apparatus from sliding forward and down when the head of the bed/gurney is elevated to fowler's position (45-60 degrees), which is the optimum position for a patient in respiratory distress. This position decreases the weight exerted on a patient's lungs thereby promoting efficient oxygenation through improved chest expansion. Fowler's position permits a patient in respiratory distress to breathe easier and more comfortably.

In the event of an emergency and immediate access to the patient is required, the entire BIANCA Box unit can be quickly pulled backwards and away from the patient and gurney at approximately a 10-15-degree angle, without difficulty or having to unlock, unhook, or unlatch any fasteners. This action is performed via the two handles located on either side of the BIANCA Box unit and allows unrestricted access to the patient within (2) seconds.

This proprietary fastening system attaches to all types of ambulance cots (including FERNO®& Stryker®), gurneys, stretchers, and hospital beds. In summary, the UGFS allows the BIANCA Box or other attached apparatus, to be safely operated during transport with or without a patient, decreasing chances of injury to the patient, operator, first responder, or healthcare provider.

The UGFS also increases structural support for the attached BIANCA Base or other apparatus by providing additional rigidity to the frame which decreases the effect of torsional forces exerted upon it. This additional rigidity in the BIANCA Base translates to increased structural support to the flexible and highly impact resistant polycarbonate panels that comprise the BIANCA Box.

The UGFS can also be used in non-mobile applications, such as a stationary bed, or any place where stability and quick access are required. The length of the slotted adjustable tension plates can be increased or decreased as necessary to accommodate various thickness requirements. The size of the UGFS can be scaled to accommodate smaller or larger applications, including mobile or non-mobile. The UGFS may also be applied vertically with modifications.

The BIANCA Anchor and Brace 1300 may be attached to the BIANCA Base as a universal gurney fastening system, comprising of two main components, the BIANCA Anchor and Brace. Together, the BIANCA Anchor and Brace allow the BIANCA Box unit to be quickly and non-permanently (without the use of a clamp, latch, lock, hook, cable, or any other semi-permanent/permanent fastening mechanism) attached to most gurneys and hospital beds, allowing it to be safely used during transport of a patient, which decreases chances of injury to the patient, first responder, and healthcare provider. Its design allows the BIANCA Box and Base to be completely and immediately pulled away from the gurney and patient in the event of an emergency. This is achieved by having the operator grasp the L-Shaped handles found on both sides of the BIANCA Box unit. The BIANCA Anchor and Brace are two separate pieces that are designed to interlock and be welded permanently together. The BIANCA Anchor is quickly installed by wedging the anchor plate underneath the gurney or hospital bed mattress at the top towards where the patient head will be located, while the BIANCA Brace captures the frame of the gurney or hospital bed underneath.

In the event of an emergency and immediate access to the patient is required, the BIANCA box can be quickly pulled backwards and away from the patient/gurney at about a 15-degree angle, via the two L-shaped handles located on either side, thus allowing unrestricted access to the patient within two seconds. This is accomplished because the anchor plate sits in between the gurney or hospital mattress and the frame of the bed/gurney, utilizing the weight of the patient's upper body to apply downward pressure on the Anchor, sandwiching it between the mattress and frame. Therefore, when the anchor plate and brace is pulled backwards and away from the top of the gurney/hospital bed, it is free to slide out without having to loosen any fastener or connections. This unique safety design of the BIANCA Anchor and Brace together, allow for the security and stability of the BIANCA Box unit on the gurney, while also prioritizing the patient's safety in the event of an emergency.

The BIANCA Anchor and Brace are directly attached to the tubular pivoting crossbar (with two locking thumb screws) that is fixed to two slotted adjustable tension plates (one found per side). The slots in these adjustable tension plates correspond with the threads of two locking tension knobs, found on each side of the BIANCA Base. Tightening of these locking tension knobs, ultimately affixes the BIANCA Anchor and Brace to the BIANCA Base.

The BIANCA Anchor 1301 may include an anchor plate as an aluminum plate (could be titanium or stainless steel in the future for increased strength, durability, and reduction in weight) that is specifically designed to slide in between the mattress and metal frame of a gurney, ambulance cot, or hospital bed. Because it is attached to the BIANCA Box above, it is subjected to left and right twisting motions which could cause deformity to its shape. The shape of the anchor plate is designed to withstand torsional forces from all directions to keep it straight and aligned flat in between the mattress and its frame. It has a rounded shape at the end which allows it to be wedged like a plate, in between the mattress and frame. Some ambulance cots have shoulder straps that anchor at the top of where the shoulders are normally located (when the patient is laying flat) into the frame beneath it. This causes an issue for a large plate to be inserted without interfering with the safety points/anchors where the shoulder straps attach. The BIANCA Anchor plate solves this issue with its rounded design and tapered sides, allowing the plate to be inserted in between the shoulder straps without affecting the safety harness that secures the patient to the frame of ambulance cot during transport.

The size and location of the BIANCA Anchor plate is designed to directly correspond with the patient's head and shoulder region on the top side of the mattress. This design utilizes the upper body weight of the patient to keep the BIANCA Box unit stable. The patient's weight keeps the mattress down, which keeps the BIANCA Anchor plate flat and flush with the mattress and ambulance cot frame. The anchor plate prevents the BIANCA Box unit from shifting back and forth, wobbling up and down, and swaying left to right while it is fully assembled on the gurney or hospital bed. The BIANCA Anchor is wedged in between the mattress that the patient lays on, and the frame of the hospital bed or gurney. The downforce exerted by the weight of the patient's upper body is translated to the mattress, which keeps the anchor plate flat and flush with the gurney or hospital bed frame. With the anchor plate flat, the tubular pivoting crossbar and all attached components including the BIANCA Base and BIANCA Box are also maintained flat and flush with the gurney or hospital bed frame. Furthermore, the anchor plate has a slot in the center that interlocks with the center safety catch, which is an extension from the center backing plate of the BIANCA Base. Once interlocked, and the patient is strapped down, and the two locking thumb screws are tightened, the BIANCA Box unit cannot be rotated backwards due to the BIANCA Anchor and Brace capturing the gurney or hospital bed frame. The interlocking of these two pieces prevents the entire unit from flipping backwards and off the gurney or hospital bed preventing any possible injury or harm to the operators or patient. This safety feature prevents unintentional movement of the box while it is fully deployed with the patient inside the BIANCA Box.

The outer edge of the BIANCA Anchor is lined with high-temperature silicone rubber for edge protection and add friction between the mattress above and metal frame below it, which decreases sliding around during transport.

The BIANCA Brace 1302 used in conjunction with the anchor plate encases the top portion of the gurney or hospital bed's structural frame (towards the side of the patient's head), preventing the box from being unintentionally flipped backwards and off the patient while it is in use. It prevents the BIANCA Box unit from shifting weight left or right because it encompasses the frame of the gurney or hospital bed. The BIANCA Brace also assists with providing lateral stability by decreasing the amount of side-to-side rocking that may occur due to shifting of the patient's weight during transport, especially with the head of the gurney or bed elevated to Fowler's position. The BIANCA Anchor and Brace are fixed to the tubular pivoting crossbar in the center.

The BIANCA Brace begins as a flat sheet of metal that is designed to be bent at a 90-degree angle, creating an L-shape with a minimum inner height of one and a half inches. This new L-shaped brace is interlocked and welded to the BIANCA Anchor. Once these two pieces are permanently interlocked together, a C-Channel is formed. This C-Channel will have a minimum gap of 1.5" to accommodate a variety of gurney or hospital metal bed frames. The C-Channel effectively wraps around 75% of the square or tubular metal frame of the gurney or hospital bed, limiting its mobility and the directions that it can move in. The C-Channel effectively only allows movement in one direction, which when mounted at the head of the gurney/bed is backwards towards the operator of the BIANCA Box unit. The brace functions like a hook and prevents the BIANCA Box unit from sliding forward and down when the head of the gurney or hospital bed is elevated to fowler's position, which allows the patient to sit upright and breathe more comfortably.

The center safety catch 1303 (backing plate extension from BIANCA Base that interlocks with the BIANCA Anchor) may be an aluminum lip that extends downward from the BIANCA Base's backing plate and catches the head of the mattress. This prevents the box from moving forward when the head of the gurney or hospital bed is elevated to fowler's position, allowing the patient to sit upright and breathe more comfortably while maintaining enclosure integrity. The center safety catch also interlocks with a slot in the BIANCA Anchor, preventing the entire BIANCA Box unit from rotating backwards off of the gurney or hospital bed.

The (2) Safety skid plates 1304 (attached to BIANCA Base) may be found towards the patient side, and on both sides of the BIANCA Base are two gurney skid plates which hug the gurney mattress from both sides, keeping the box aligned with the mattress and preventing the box from sliding left to right (side to side) during transport or if the box is accidentally jarred during use. These mounts are lined with silicone rubber to provide additional friction against the cloth-like/textured material of the mattress, decreasing any unwanted movement of the unit.

The tubular pivoting crossbar 1305 with two (2) locking thumb screws (see below) is described next. The tubular pivoting crossbar is made up of a smaller diameter, stainless steel, inner tube with a marginally larger diameter, aluminum, outer tube which encases the inner tube like a sheath with approximately a small air gap in between the two tubes. The stainless steel inner tube is permanently affixed to the stainless steel, slotted adjustable tension plates on both ends, while the aluminum outer tube is permanently affixed to the backside of the aluminum BIANCA Anchor and Brace in the center. The small air gap in between the two tubes allows the outer tube to freely pivot 360 degrees around the inner tube, unobstructed. The stainless steel, slotted adjustable tension plates are attached to the BIANCA Base via the locking tension knobs which travel through their slots and ultimately threaded into the nuts located in inferior support of the BIANCA Base. The purpose of this pivoting mechanism is to allow the operator of the BIANCA Box unit to easily maneuver and slide the attached BIANCA Anchor plate in between the gurney or hospital bed mattress and its frame.

Only the outer aluminum tube has two evenly spaced holes with a diameter that corresponds with the threaded inner diameter of two nuts that have been welded on the outside. Two locking thumbscrews are threaded through these nuts and when tightened down, the outer aluminum tube no longer pivots freely around the inner tube and is locked in place until loosened. Unlocking of these locking thumbscrews, allows the BIANCA Anchor and Brace to be freely maneuvered to accommodate differences between various ambulance cots, gurneys, or hospital bed manufacturers.

The (2) Locking thumb screws 1305a is described next. Two red thumb screws located on the tubular pivoting crossbar that connects the BIANCA Anchor and Brace to the BIANCA Base. These need to be tightened once the box is fully assembled on the gurney, to prevent the outer tube from unwanted pivoting around the inner tube while the BIANCA Box unit is in use. Tightening of these two red thumb screws as well as the two locking tension knobs that are on both sides of the BIANCA Base, keeps the base and box sturdily attached to the gurney or hospital bed while it is in transport.

The (2) Slotted adjustable tension plates 1306 is described next. Two slotted stainless steel plates are fixed to the tubular pivoting crossbar, with one on each side. The slots in the center of the plate run almost the entire length of the plate and its width corresponds with the thread thickness of the locking tension knobs. The length of the slot allows the BIANCA Anchor and Brace to accommodate various mattress heights. To accommodate a thicker mattress, the entire anchor and brace unit can be slid downward, widening the gap between the anchor plate and the bottom of the BIANCA Base. If a thinner mattress is utilized, then the entire anchor and brace can be slid upward, narrowing the gap between the anchor plate and the bottom of the BIANCA Base. This mechanism attaches the BIANCA Anchor and Brace system to the BIANCA Base and allows the operator to adjust the UGFS to accommodate varying mattress thicknesses. Once the desired mattress thickness is adjusted for, the system is locked in place by tightening the two locking tension knobs, on either side of the BIANCA Base. This ensures that the distance between the bottom of the BIANCA Base and the BIANCA Anchor plate remains exactly where they need to at all times, so that the BIANCA Box does not lift away from the BIANCA Anchor and Brace if the gurney goes over a bump, or the ambulance it is being transported in, goes over a bump in the road.

Adjusting locking tension knobs allows the operator to compensate for the different thicknesses found on a wide variety of gurney/hospital bed mattresses that the BIANCA Box can be installed on. Most standard gurneys have a 2" thick mattress, while most hospital beds have a 5-6" thick mattress, both of which can easily be accommodated.

The (2) Locking tension knobs 1307 are described next. Two studded tension knobs, one on each side of the BIANCA Base, are passed through the slot in the adjustable tension plates and are threaded into nuts located on the inferior support of the BIANCA Base. The location of these nuts are aligned at specific points so that when the locking tension knobs are tightened, the following occur: the BIANCA Anchor interlocks with the Center safety catch and together the BIANCA Anchor and Brace lie flush with the gurney or hospital mattress and its metal frame.

These two locking tension knobs must be engaged prior to operation of the BIANCA Box or movement of the gurney or hospital bed, in order to ensure that the BIANCA Box unit is properly secured to the frame of the gurney or hospital bed. These locking tension knobs are not required to be loosened prior to emergency removal of the BIANCA Box unit. The knobs can also be handles, star grips, knurled grips, or any type of component that provides leverage.

In some embodiments, the UGFS may permit:
1. Quick attachment to gurneys, stretchers, hospital beds, and ambulance cots with various mattress heights ranging from 2-6"
2. Safe operation while maneuvering the ambulance cot, gurney/stretcher, or hospital bed during patient transport
3. Immediate patient access in the event of an emergency without having to unhook, unlock, unclamp, unlatch any fasteners or use of any other permanent/semi-permanent fastening mechanism.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

What is claimed is:

1. A collapsible isolation apparatus used for treating a person, the collapsible isolation apparatus comprising:
   a collapsible frame comprising a base and a plurality of rigid or soft panel elements at least partially enclosing a volume of space, wherein each of the plurality of rigid or soft panel elements is foldably hinged to at least one of the base or another of the rigid or soft panel elements, and wherein at least one panel element of the plurality of rigid or soft panel elements comprises an open space for mounting a motor for moving air;

a mounting system attached to the base, the mounting system comprising:
  a coupling anchor plate with a slot,
  a brace for securing the apparatus to a patient transportation device,
  a center safety catch comprising a backing plate extension from the base, wherein the backing plate extension interlocks with the slot of the coupling anchor plate, wherein the brace interlocks to the anchor plate forming a C-channel that provides a interconnection to the patient transportation device,
  at least two safety skid plates attached to the base of the apparatus on opposing sides of the base;
  a tubular pivoting crossbar with at least two fastening screws, wherein the fastening screws are located on the crossbar that connects the anchor plate and the brace to the base;
  at least two slotted adjustable tension plates fixed to the tubular pivoting crossbar one on each opposing side of the crossbar, wherein the anchor plate and the brace are directly attached to the tubular pivoting crossbar with the at least two fastening screws, wherein the crossbar is fixed to the two slotted adjustable tension plates; and
  at least two locking tension knobs, wherein the slotted adjustable tension plates are attached to the base via the locking tension knobs,
  wherein the tubular pivoting crossbar includes an outer tube which encases coaxially an inner tube in a manner allowing an air gap in between the outer tub and the inner tube that permit the crossbar to pivot, wherein the inner tube is permanently affixed to the slotted adjustable tension plates at both ends of the tubular pivoting crossbar, while the outer tube is permanently affixed to a backside of the anchor plate and the brace.

2. The collapsible isolation apparatus of claim 1, wherein each of a left side panel element, a right side panel element, and a rear panel element is foldably hinged to the base,
  and wherein the rear panel element is foldably hinged to a top panel element.

3. The collapsible isolation apparatus of claim 1, wherein the rear panel element comprises an access port including a flap that swings open and closed by a hinged joint, the access port configured for an operator to provide medical care to the person within the collapsible isolation apparatus.

4. The collapsible isolation apparatus of claim 1, wherein each of the plurality of rigid or soft panel elements comprise substantially translucent surfaces.

5. The collapsible isolation apparatus of claim 4 further comprising at least one air filter coupled to the motor.

6. The collapsible isolation apparatus of claim 4, wherein the motor comprises a high-efficiency particulate air (HEPA) filter motor.

7. The collapsible isolation apparatus of claim 1, wherein the patient transportation device is one of a gurney, a stretcher, a hospital bed, a surgical bed, an ambulance cot, or a similar four-wheeled device with a mattress and frame.

8. The collapsible isolation apparatus of claim 1, further comprising an intravenous (IV) pole coupled to the base for attaching to an IV bag.

9. The collapsible isolation apparatus of claim 1, wherein the collapsible frame comprises an open side without a panel element, and
  wherein the collapsible isolation apparatus further comprises a flexible transparent cover enclosing most or substantially all of the open side.

10. A method for treating a person using a collapsible isolation apparatus, the method comprising:
  providing the collapsible isolation apparatus, the apparatus comprising:
  a collapsible frame comprising a base and a plurality of rigid or soft panel elements at least partially enclosing a volume of space, wherein each of the plurality of rigid or soft panel elements is foldably hinged to at least one of the base or another of the rigid or soft panel elements, and wherein at least one panel element of the plurality of rigid or soft panel elements comprises an open space for mounting a motor for moving air; and
  a mounting system attached to the base, the mounting system comprising:
  a coupling anchor plate with a slot,
  a brace for securing the apparatus to a patient transportation device,
  a center safety catch comprising a backing plate extension from the base, wherein the backing plate extension interlocks with the slot of the coupling anchor plate, wherein the brace interlocks to the anchor plate forming a C-channel that provides an interconnection to the patient transportation device,
  at least two safety skid plates attached to the base of the apparatus on opposing sides of the base;
  a tubular pivoting crossbar with at least two fastening screws, wherein the fastening screws are located on the crossbar that connects the anchor plate and the brace to the base;
  at least two slotted adjustable tension plates fixed to the tubular pivoting crossbar one on each opposing side of the crossbar, wherein the anchor plate and the brace are directly attached to the tubular pivoting crossbar with the at least two fastening screws, wherein the crossbar is fixed to the two slotted adjustment tension plates;
  wherein the tubular pivoting crossbar includes an outer tube which encases coaxially an inner tube in a manner allowing an air gap in between the outer tube and the inner tube that permit the crossbar to pivot, wherein the inner tube is permanently affixed to the slotted adjustable tension plates at both ends of the tubular pivoting crossbar, while the outer tube is permanently affixed to a backside of the anchor plate and the brace; and
  at least two locking tension knob, wherein the slotted adjustable tension plates are attached to the base via the locking tension knobs;
  assembling the collapsible isolation apparatus by folding out the plurality of rigid or soft panel elements into an assembled configuration;
  providing the person treatment using the collapsible isolation apparatus in the assembled configuration; and
  placing and orienting the person within the collapsible isolation apparatus in the assembled configuration.

11. The method of claim 10, further comprising:
  securing an intravenous (IV) pole to the collapsible isolation apparatus,
  mounting an IV bag to the IV pole; and
  providing hydration to the person by coupling a tube from the IV bag to the person.

12. The method of claim 10, further comprising attaching a flexible transparent cover enclosing most or substantially all of an open side of the collapsible isolation apparatus.

13. The method of claim 10, wherein the patient transportation device is one of a gurney, a stretcher, a hospital bed, a surgical bed, an ambulance cot, or similar four-wheeled device with a mattress and frame.

14. The method of claim 10, further comprises attaching the apparatus to the patient transportation device.

\* \* \* \* \*